(12) United States Patent  
Jaenisch

(10) Patent No.: US 7,945,105 B1  
(45) Date of Patent: May 17, 2011

(54) AUTOMATED TARGET SHAPE DETECTION FOR VEHICLE MUON TOMOGRAPHY

(75) Inventor: Holger M. Jaenisch, Toney, AL (US)

(73) Assignee: Decision Sciences International Corporation, Poway, CA (US)

(*) Notice: Subject to any disclaimer, the term of this patent is extended or adjusted under 35 U.S.C. 154(b) by 511 days.

(21) Appl. No.: 12/099,072

(22) Filed: Apr. 7, 2008

(51) Int. Cl.
*G06K 9/36* (2006.01)

(52) U.S. Cl. .......................... 382/249; 382/128; 382/254

(58) Field of Classification Search .................. 250/306, 250/307; 382/249, 128, 254
See application file for complete search history.

(56) References Cited

U.S. PATENT DOCUMENTS

| | | | |
|---|---|---|---|
| 5,732,158 | A | 3/1998 | Jaenisch |
| 6,169,476 | B1 | 1/2001 | Flanagan |
| 6,930,596 | B2 | 8/2005 | Kulesz et al. |
| 7,119,676 | B1 | 10/2006 | Silverstrim et al. |
| 7,327,913 | B2 | 2/2008 | Shpantzer et al. |
| 7,426,035 | B2 | 9/2008 | Shpantzer |
| 7,470,905 | B1 | 12/2008 | Goldberg et al. |
| 7,483,600 | B2 | 1/2009 | Achiam et al. |
| 7,488,934 | B2 | 2/2009 | Bryman |
| 7,502,118 | B2 | 3/2009 | Shpantzer |
| 7,531,791 | B2 | 5/2009 | Bryman |
| 7,652,254 | B2 | 1/2010 | Shpantzer et al. |
| 2004/0096143 | A1 | 5/2004 | Shpantzer et al. |
| 2005/0088299 | A1 | 4/2005 | Bandy et al. |
| 2006/0002368 | A1 | 1/2006 | Budampati et al. |
| 2006/0180753 | A1 | 8/2006 | Bryman |
| 2007/0102648 | A1 | 5/2007 | Shpantzer et al. |
| 2007/0115475 | A1 | 5/2007 | Shpantzer |
| 2007/0127030 | A1 | 6/2007 | Shpantzer |
| 2007/0133918 | A1 | 6/2007 | Cho et al. |
| 2007/0140613 | A1 | 6/2007 | Achiam et al. |
| 2008/0025728 | A1 | 1/2008 | Shpantzer et al. |
| 2008/0128604 | A1 | 6/2008 | Bryman |
| 2008/0159758 | A1 | 7/2008 | Shpantzer et al. |
| 2008/0212970 | A1 | 9/2008 | Shpantzer |
| 2008/0258880 | A1 | 10/2008 | Smith et al. |
| 2008/0315091 | A1* | 12/2008 | Morris et al. ................. 250/307 |
| 2009/0224157 | A1 | 9/2009 | Goldberg et al. |
| 2009/0295576 | A1 | 12/2009 | Shpantzer et al. |
| 2010/0065745 | A1 | 3/2010 | Goldberg et al. |

FOREIGN PATENT DOCUMENTS

| | | | |
|---|---|---|---|
| WO | WO2008118209 | A3 | 10/2002 |
| WO | WO2008086507 | A1 | 7/2008 |
| WO | WO2008118208 | A3 | 10/2008 |
| WO | WO2008123892 | A9 | 10/2008 |
| WO | WO2008140559 | A2 | 11/2008 |
| WO | WO2008140560 | A3 | 11/2008 |

OTHER PUBLICATIONS

Frühwirth, R., "Application of Kalman filtering to track and vertex fitting," Nuclear Instruments and Methods in Physics Research Section A, 262(2-3):444-450, Dec. 1987.

(Continued)

*Primary Examiner* — Kiet T Nguyen
(74) *Attorney, Agent, or Firm* — Perkins Coie LLP

(57) ABSTRACT

Techniques, apparatus and systems for muon tomography vehicle imaging use autonomous processing of 3-dimensional muon tomography vehicle images based on Data Modeling techniques and various applications including analyzing vehicle voxel data such as muon vehicle images to detect potential threat objects and then to further discriminate the identified potential threat objects by shape.

25 Claims, 10 Drawing Sheets
(4 of 10 Drawing Sheet(s) Filed in Color)

OTHER PUBLICATIONS

Hardin, W., "Muon imager searches for smuggled nuclear material," Proceedings of SPIE, the International Society for Optical Engineering, 3(9):5-6, Sep. 2003.

International Preliminary Report on Patentability dated Jul. 14, 2009 for International Application No. PCT/US2008/050819, filed Jan. 10, 2008 (5 pages).

International Search Report and Written Opinion dated Jun. 18, 2008 for International Application No. PCT/US2008/050819, filed Jan. 10, 2008 (7 pages).

Jaenisch, H.M., et al., "Data Modeling for Defense Planning," Society for Computer Simulation (Huntsville Simulation Conference 2003), Huntsville, AL, 6 pages, Oct. 30-31, 2003.

Jaenisch, H.M., et al., "Data Modeling for Radar Applications," Proceedings of IEEE Radar Conference, pp. 379-386, May 2003.

Jaenisch, H.M., et al., "Enabling Human HUMS with Data Modeling," Proc. SPIE—Defense and Security Symposium, 12 pages, Apr. 2006.

Jaenisch, H.M., et al., "Enabling Unattended Data Logging and Publication by Data Model Change Detection and Environmental Awareness," Proc. SPIE—Defense and Security Symposium, vol. 6231, 62310R, 11 pages, Apr. 2006.

Jaenisch, H.M., et al., "Muon Imaging and Data Modeling," Proceedings of SPIE, the International Society for Optical Engineering, 6538(85):1-8, Apr. 2007.

Jaenisch, H.M., et al., "A Simple Algorithm For Sensor Fusion Using Spatial Voting (Unsupervised Object Grouping)," Proceedings of SPIE—Defense and Security Symposium, 6968(68):696804.1-696804.12, Mar. 2008.

Jenneson, P.M., "Large Vessel Imaging Using Cosmic-Ray Muons," Nuclear Instruments and Methods in Physics Research A, 525(1-2):346-351, Jun. 2004.

Pooley, J., et al., "Fault Detection via Complex Hybrid Signature Analysis," JANNAF 39th Combustion, 27th Airbreathing Propulsion, 21st Propulsion Systems Hazards, and 3rd Modeling and Simulation Subcommittees Joint Meeting, Colorado Springs, CO, 11 pages, Dec. 2003.

Priedhorsky, W.C., et al., "Detection of High-Z Objects Using Multiple Scattering of Cosmic Ray Muons," Review of Scientific Instruments, 74(10):4294-4297, Oct. 2003.

Schultz, L., et al., "Statistical Reconstruction for Cosmic Ray Muon Tomography," IEEE Transactions on Image Processing, 16(8):1985-1993, Aug. 2007.

* cited by examiner

Exposure Time: 15 Sec.

Exposure Time: 30 Sec.

Exposure Time: 60 Sec.

| NSqr/NSrf | NCir/NSrf | NRect/NSrf | Shape | |
|---|---|---|---|---|
| 0 | 1 | 0 | 1 | iclass=1 is Shell |
| 1 | 0 | 0 | 1 | iclass=2 is Cylindrical |
| 1 | 0 | 1 | 1 | iclass=3 is Elongated Box-like |
| 0 | 1 | 0 | 2 | iclass=4 is Spherical |
| 0 | 0.6 | 0.4 | 2 | iclass=5 is Unrecognized (Possibly Multiple) |
| 0 | 0.66666667 | 0.33333333 | 2 | |
| 0 | 0.71428571 | 0.28571429 | 2 | |
| 0 | 0.75 | 0 | 3 | |
| 0.22222222 | 0 | 0.44444444 | 3 | |
| 0.2 | 0 | 0.6 | 3 | |
| 0.18181818 | 0 | 0.54545455 | 3 | |
| 0.28571429 | 0 | 0.71428571 | 3 | |
| 0.66666667 | 0 | 0.66666667 | 3 | |
| 0.11111111 | 0.11111111 | 0 | 4 | |
| 0.2 | 0.06666667 | 0.4 | 4 | |
| 0.33333333 | 0 | 0 | 5 | |
| 0.4 | 0.4 | 0 | 5 | |
| 0.4 | 0 | 0 | 5 | |

FIG. 9

AUTOMATED TARGET SHAPE DETECTION FOR VEHICLE MUON TOMOGRAPHY

BACKGROUND

This application relates to techniques, apparatus and systems for vehicle muon tomography imaging.

Muon tomography is an imaging technique that produces an image of an object such as a vehicle or its contents based on detection of the scattering of cosmic ray produced muons as they pass through the object. Muons scattered by an object can be detected and the detected signals can be processed to provide specific density and three-dimensional imaging of materials.

The collision of natural cosmic rays with atoms in the earth's upper atmosphere creates unstable particles, such as pions and kaons, which decay to muons. Muons penetrate through the atmosphere and into the ground at the rate of approximately 1 per square centimeter per minute. Muons can be thought of as much larger cousins of the electrons that are an essential part of ordinary matter. Energetic muons interact strongly enough with matter by ionization to be easily detected, and can penetrate large thicknesses without significant impairment.

Physicists at the Los Alamos National Laboratory (LANL) have developed techniques for detecting scattering of cosmic ray produced muons to produce tomographic images of an object exposed to the cosmic ray muons. See, e.g., Priedhorsky et al., "Detection of high-Z objects using multiple scattering of cosmic ray muons", Proceedings of SPIE Press, Vol. 5199A-39 (August, 2003). As a muon moves through material, Coulomb scattering of the charges of subatomic particles perturb its trajectory. The total deflection depends on several material properties, but the dominant parameters are the atomic number, Z, of the nuclei and the material density. The LANL techniques are based on precise reconstruction of individual muon tracks and are capable of detecting and visually representing potential threat objects in vehicles or transportable containers in order to alert responsible authorities, thereby allowing them to preemptively interdict the movement of such material to prevent any damage and destruction. A vehicle muon tomography system can be constructed based on the LANL techniques to provide hazard detection at various locations including ports and checkpoints. For example, such systems can provide the Department of Homeland Security (DHS) with an effective solution to the critical need for timely vehicle and cargo inspection nationwide.

Various aspects of muon tomography imaging techniques are described in literature. See, e.g., Jenneson, "Large vessel imaging using cosmic-ray muons", Nuclear Instruments and Methods in Physics Research Section A: Accelerators, Spectrometers, Detectors and Associated Equipment, Volume 525, Issues 1-2, Pages 346-351, Proceedings of the International Conference on Imaging Techniques in Subatomic Physics, Astrophysics, Medicine, Biology and Industry (June, 2004); and "Muon imager searches for smuggled nuclear material", OE magazine, SPIE (September, 2003).

SUMMARY

This specification describes techniques, apparatus and systems for vehicle muon tomography imaging using autonomous processing of 3-dimensional (3D) muon tomography vehicle images based on Data Modeling techniques and various applications including analyzing vehicle voxel data such as muon vehicle images to detect potential threat objects within a vehicle or transportable container and then to further discriminate the identified potential threat objects by shape.

In one aspect, a computer-automated method for processing muon vehicle imaging data of a vehicle inspection region within a vehicle muon tomography imaging system is described. This method includes processing muon vehicle imaging data obtained from the vehicle inspection region to obtain a histogram of the muon vehicle imaging data at different positions in the vehicle inspection region; separating the muon vehicle imaging data into bins based on the histogram; removing a subset of the muon vehicle imaging data in a mode bin that has higher frequencies of occurrence than remaining muon vehicle imaging data from the muon vehicle imaging data to retain the remaining muon vehicle imaging data for further processing; determining an optimal number of bins for separating the remaining muon vehicle imaging data into data bins; processing the remaining muon vehicle imaging data to obtain a histogram of the remaining muon vehicle imaging data at different positions in the vehicle inspection region; separating the remaining muon vehicle imaging data into data bins at the optimal number of bins; and removing data in a mode bin that has higher frequencies of occurrence than the rest of the remaining muon vehicle imaging data to retain remaining muon vehicle imaging data as target detection data for further processing. This method also includes using a background recognizer Data Model for identifying background vehicle structure from the target detection data; applying the background recognizer Data Model to process the remaining muon vehicle imaging data to produce an image of the vehicle inspection region by removing background structure; using a target identification Data Model for identifying a target object from the target detection data; applying the target identification Data Model to process data of the image produced after applying the background recognizer Data Model to produce an image of the target object; and processing the image of the target object to determine a location and a shape of the target object in the vehicle inspection region.

In another aspect, a computer system for processing muon vehicle imaging data of a vehicle inspection region within a muon tomography vehicle imaging system is described. This system includes means for processing muon vehicle imaging data obtained from the vehicle inspection region to obtain a histogram of the muon vehicle imaging data at different positions in the vehicle inspection region; means for separating the muon vehicle imaging data into bins based on the histogram; means for removing a subset of the muon vehicle imaging data in a mode bin that has higher frequencies of occurrence than remaining muon vehicle imaging data from the muon vehicle imaging data to retain the remaining muon vehicle imaging data for further processing; means for determining an optimal number of bins for separating the remaining muon vehicle imaging data into data bins; means for processing the remaining muon vehicle imaging data to obtain a histogram of the remaining muon vehicle imaging data at different positions in the vehicle inspection region; means for separating the remaining muon vehicle imaging data into data bins at the optimal number of bins; and means for removing data in a mode bin that has higher frequencies of occurrence than the rest of the remaining muon vehicle imaging data to retain remaining muon vehicle imaging data as target detection data for further processing. This system also includes means for using a background recognizer Data Model for identifying background structure from the target detection data; means for applying the background recognizer Data Model to process the target detection data to produce an image of the vehicle inspection region by removing identified background structure; means for using a target identification Data Model for identifying a target object from the target detection data; means for applying the target identification Data Model to process data of the image produced after applying the background recognizer Data Model to produce an image of the target object; and means for processing the image of the target object to determine a location and a shape of the target object in the vehicle inspection region.

In another aspect, a muon tomography vehicle imaging system is described to include a first set of muon detectors located on a first side of a vehicle inspection region holding a vehicle for inspection, the muon detectors measuring incident muons; a second set of muon detectors located on a second side of the vehicle inspection region opposite to the first side to measure outgoing muons exiting the vehicle inspection region; and a muon tomography control module that receives detector outputs from the first and the second set of muon detectors and processes the detector outputs to produce a 3-dimensional image of the vehicle inspection region. The muon tomography control module includes a suspect object detection module for processing muon vehicle imaging data of the 3-dimensional image. The suspect object detection module includes means for applying Data Models to process the muon vehicle imaging data to isolate one or more target objects from other objects in the vehicle inspection region; means for applying primitive shape recognition to cross-section slices of an image of a volume containing data points of the one or more target objects to identify predetermined primitive shapes; and means for processing identified primitive shapes to construct a 3-dimensional image of each target object.

In another aspect, a computer-automated method for processing muon vehicle imaging data from a muon tomography vehicle imaging system is described to include applying Data Models to process muon tomography vehicle image data to isolate one or more target objects from other objects in a volume under inspection by the muon tomography vehicle imaging system; applying primitive shape recognition to cross-section slices of an image of the volume containing data points of the one or more target objects to identify predetermined primitive shapes; and processing identified primitive shapes to construct a 3-dimensional image of each target object.

In yet another aspect, a computer-implemented method for using natural cosmic muons as a radiation source to obtain muon tomographic images of a vehicle under inspection is described to include obtaining a cosmic muon tomography vehicle image of a vehicle under inspection; processing vehicle voxel data of each obtained muon vehicle image to compute histogram of the vehicle voxel data of the obtained muon vehicle image; applying statistical processing based on the histogram to the vehicle voxel data to generate a Data Model to monitor one or more changes in the obtained muon vehicle image indicative of presence of a target object in the obtained muon vehicle image; and determining a shape of the target object.

Particular embodiments described in this specification can be implemented to realize one or more of advantages. For example, a threat object can be identified by autonomous processing without human intervention. Suitable Data Modeling based on statistical process can provide efficient and robust data processing and provide autonomous identification of the shape of a threat object. As another example, the present Data Modeling allows for relatively short muon vehicle imaging exposure times in capturing the muon vehicle imaging data without compromising the data processing accuracy and thus allows for high-speed detection.

The details of one or more embodiments of the invention are set forth in the accompanying drawings and the description below. Other features, aspects, and advantages of the invention will become apparent from the description, the drawings, and the claims.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 9 shows an example for data processing to indicate the corresponding primitive shapes for the process in FIG. 5.

Like reference numbers and designations in the various drawings indicate like elements.

DETAILED DESCRIPTION

Muons contribute roughly a tenth of the natural dose of daily ionizing radiation at the earth's surface and such radiation exposure is a natural and unavoidable feature of our environment. Muon tomography takes advantage of this universal presence and the penetrating characteristics of the muons to reveal the position and size of various materials without causing any harm to personnel or requiring additional intervention by inspectors to correctly identify potential threats. Moreover, efforts to conceal weapons or other dangerous materials by encasing them in a massive lead container would be just as revealing, since the muon deflection patterns would indicate the presence of shielding material where it didn't belong.

Figure 1:
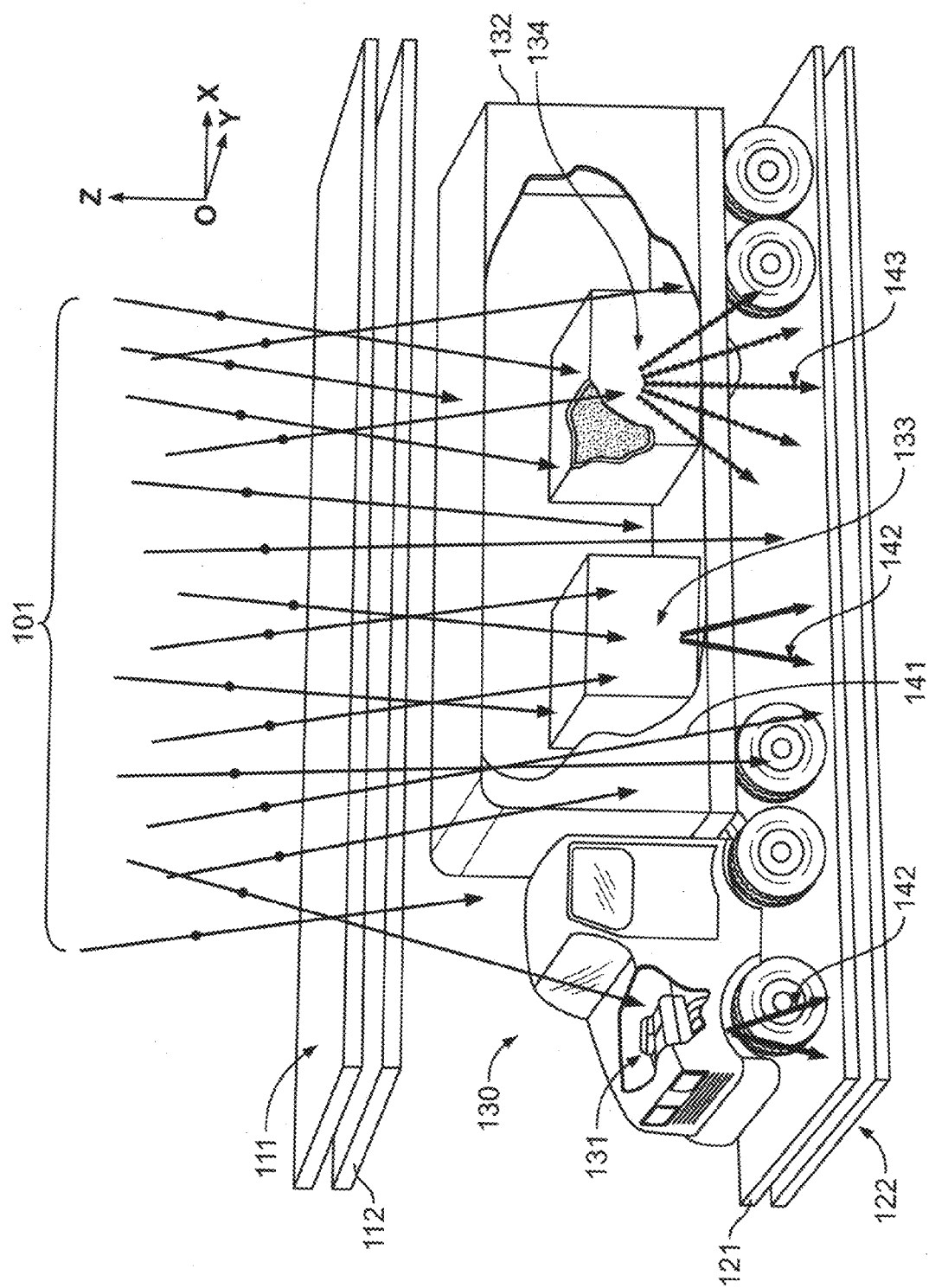
FIG. 1 illustrates an example of a muon tomography vehicle imaging system for inspecting a vehicle for other objects.

FIG. 1 illustrates an example of a muon tomography vehicle imaging system for inspecting a vehicle for other objects. This system for detecting muons includes a vehicle inspection region or volume 130 for placing a vehicle to be inspected. On the top and bottom sides of this vehicle inspection region 130, muon detectors 111, 112, 121 and 122 are provided to detect the incident muons from the atmosphere at the top of the region 130 and outgoing muons at the bottom of the region 130. Such muon detectors can be drift tubes that are filled with a gas which can be ionized by muons and are configured to collect and correlate the amount of deflection of each muon that passes through and the vehicle or container being inspected. Multiple drift tubes can be used to form detector arrays to accurately determine a muon's path and, by analyzing the amount of deflection and the pattern of the scattering which results, a visual three-dimensional image of the variety of materials can be generated.

More specifically, the muon detectors 111, 112, 121 and 122 include a first set of position-sensitive muon detectors 111 and 112 located on the top side of the vehicle inspection region 130 to measure positions and angles of incident muons, a second set of position sensitive muon detectors 121 and 122 located on the bottom side of the vehicle inspection region 130 opposite to the top side to measure positions and angles of outgoing muons exiting the vehicle inspection region. A muon tomography signal processing unit, which may include, e.g., a microprocessor, is provided to receive data of measured signals of the incoming muons from the first set of position sensitive muon detectors 111 and 112 and measured signals of the outgoing muons from the second set of position sensitive muon detectors 121 and 122.

The muon trajectories are more strongly affected by special nuclear material (SNM) and materials that make good gamma ray shielding (such as lead and tungsten) than by the materials that make up more ordinary objects (such as water, plastic, aluminum, and steel). Each muon carries information about the objects that it has penetrated, and by measuring the scattering of multiple muons, one can probe the properties of these objects. In particular, one can detect high-Z objects amongst more typical low-Z and medium-Z matter. The example in FIG. 1 shows a truck that carries a cargo 133 and a shielded crate 134 that conceals a high Z object. The incident cosmic muons 101 are scattered by the truck and everything in the truck. The degrees of scattering of the muons vary with the object or objects in the paths of the muons. For example, the muon rays 141 shown in FIG. 1 represent low scattering muon paths in which truck components or objects have low Z numbers. The truck's engine 131 tends to have higher Z than other vehicle components and thus causes mild scattering of muons as represented by the muon rays 142. The cargo 133 carried by the truck may also cause mild scattering of muons. The high Z object in the shielded crate 134 cause large scattering 143 of the muons.

The muon tomography signal processing unit for the system in FIG. 1 is configured to analyze scattering behaviors of muons, caused by scattering of the muons in the materials within the vehicle inspection region 130, based on the measured incoming and outgoing positions and angles of muons, to obtain a tomographic profile or the spatial distribution of scattering centers within the vehicle inspection region 130. The obtained tomographic profile or the spatial distribution of scattering centers can be used to reveal the presence or absence of one or more objects in the vehicle inspection region such as materials with high atomic numbers Z including nuclear materials or devices.

Notably, the image of a high Z object, such as the example enclosed in the shielded crate 134 in FIG. 1, is part of the generated muon tomography vehicle image and is mixed with images of other objects in the generated muon tomography vehicle image. One technical challenge is to fully autonomously process the muon tomography vehicle images based on computer data processing to identify a threat object in a generated muon tomography vehicle image.

Figure 2A:
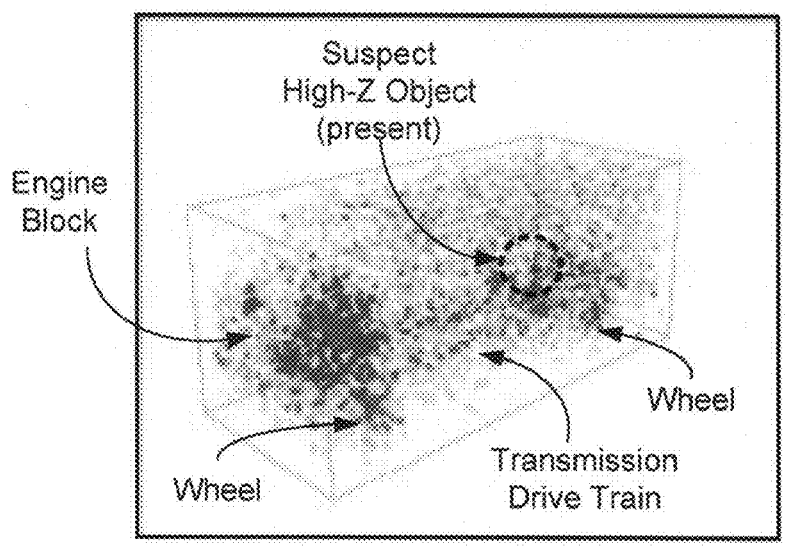
FIGS. 2A, 2B and 2C show examples of muon tomography vehicle images obtained from a LANL-built system with imaging exposure times of 15 seconds, 30 seconds and 60 seconds, respectively.
Figure 2B:
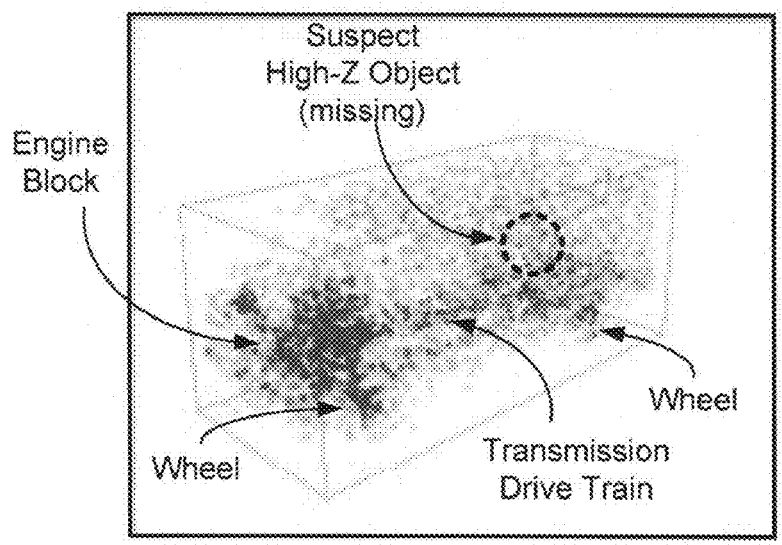
Figure 2C:
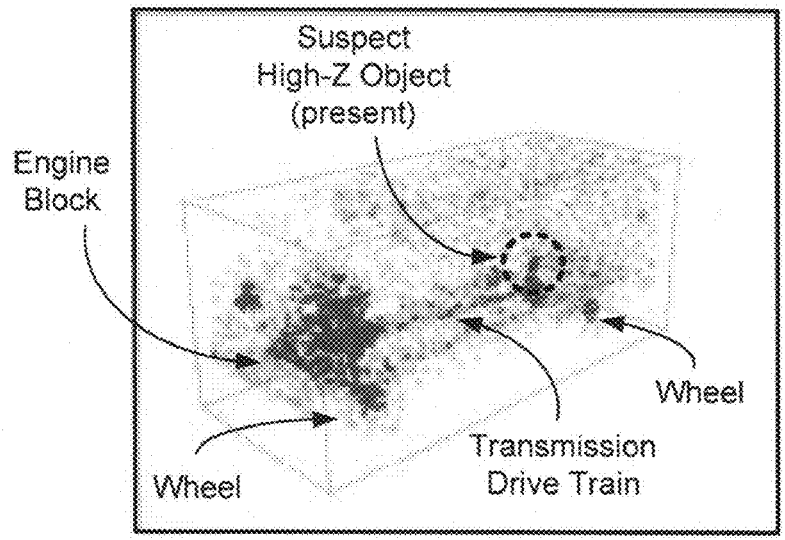

It is generally believed that longer muon vehicle imaging exposure times can improve the image quality and detection accuracy in identifying a threat object in the obtained muon tomography vehicle images. However, contrary to this general belief, longer exposure times are not necessarily better for automatic target detection, because more false positives occur. FIGS. 2A, 2B and 2C show examples of muon tomography vehicle images obtained from the LANL Large Muon Tracker system with imaging exposure times of 15 seconds, 30 seconds and 60 seconds, respectively. FIG. 2A illustrates how in as little as 15 seconds various materials and components, e.g., the engine block, transmission drive train and wheels, can be distinguished—they have been color-coded to provide a visual identification. The appearance of the small item shown in red above the rear axle and marked in a dashed line circle indicates a suspect high-Z object which can be a potential nuclear mass. However, in the image obtained with a longer exposure time of 30 seconds in FIG. 2B, the image of the suspect high-Z object is not readily visible. Therefore, muon tomography using appropriate drift tubes and advanced algorithms such as entropy based methods enables the timely inspection of all cargo entering the U.S., the monitoring of trucks and other vehicles passing through critical infrastructure points, and the detection of specific explosive components used in terrorist weapons around the world.

Techniques, apparatus and systems for muon tomography vehicle imaging can use autonomous processing of 3D muon tomography vehicle images based on discrete and analytical Data Modeling techniques comprising Entropyology or random-field-information science. These Data Modeling techniques were previously developed by Holger M. Jaenisch. These techniques may be used to analyze voxel data such as muon vehicle images to detect potential threat objects and then to further discriminate the identified potential threat objects by shape. Data Modeling uses the smallest amount of entropic information to functionally model empirical dynamics and can take the form of a group of real numbers, a single equation, or a network of equations. A Data Model can also be a variable of another function. A hierarchy of functional models (equations whose variables are themselves equations) can be built up to combine any group or subset of previously derived models. Data Modeling finds a mathematical expression that provides a good model between given finite sample values of the independent variables and the associated values of the dependent variables of the process. The predictive mathematical expression modeling the given sample of data is called a Data Model. This process involves finding both the structural form of the Data Model and the numeric coefficients for the Data Model.

The present techniques use Data Modeling methods and can be implemented in ways that minimize long exposure requirements previously reported in the literature and allow for muon vehicle imaging in the gray medium exposure length zone, which is traditionally difficult to automate. Therefore, high-speed and efficient autonomous threat detection can be achieved.

Figure 3:
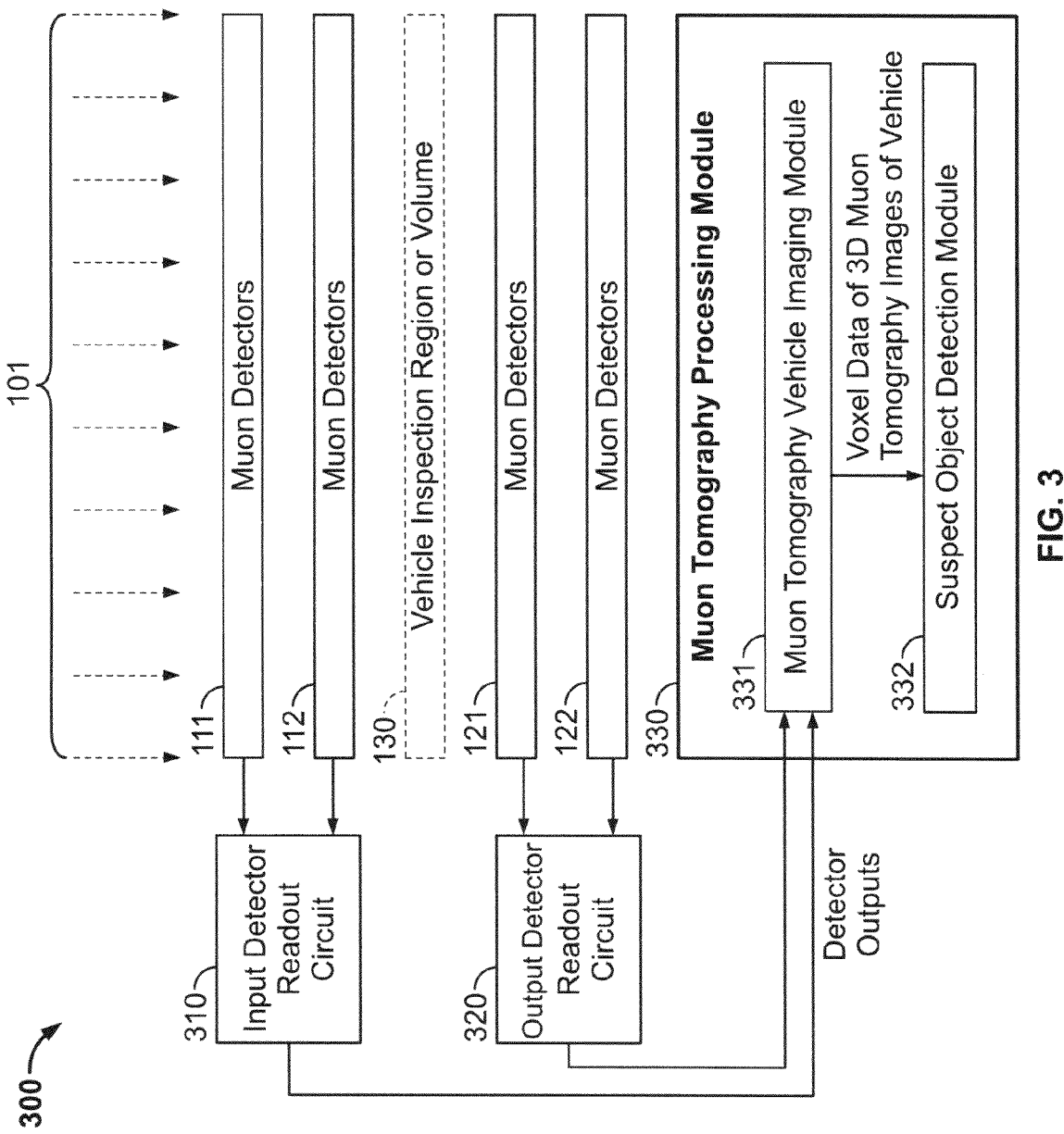
FIG. 3 shows an example of a muon tomography vehicle imaging system implementing autonomous processing of 3D muon tomography vehicle images based on Data Modeling.

FIG. 3 shows an example of a muon tomography vehicle imaging system 300 implementing autonomous processing of 3D muon tomography vehicle images based on Data Modeling. The detector design in this system 300 is based on the design in FIG. 1 and may also be implemented by other muon detector configurations. Input detector readout circuit 310 is connected to the detectors 111 and 112 to receive and pre-process the detector outputs and feeds the pre-processed detector outputs to a muon tomography processing module 330. Output detector readout circuit 320 is connected to the detectors 121 and 122 to receive and pre-process the detector outputs and also feeds the pre-processed detector outputs to the muon tomography processing module 330.

The muon tomography processing module 330 can include one or more computers or computer processors and has a muon tomography vehicle imaging processing module 331 and a suspect object detection module 332. The muon tomography vehicle imaging processing module 331 is configured to process the detector outputs from the detectors 111, 112, 121 and 122 to generate 3D muon tomography vehicle images of the vehicle inspection region 130. Examples of such images are shown in FIGS. 2A, 2B and 2C. The suspect object detection module 332 receives the voxel data of the 3D muon tomography vehicle images output by the muon tomography vehicle imaging processing module 331 and is programmed to autonomously process 3D muon tomography vehicle images based on Data Modeling. The following sections describe details of operations of the suspect object detection module 332.

Figure 4:
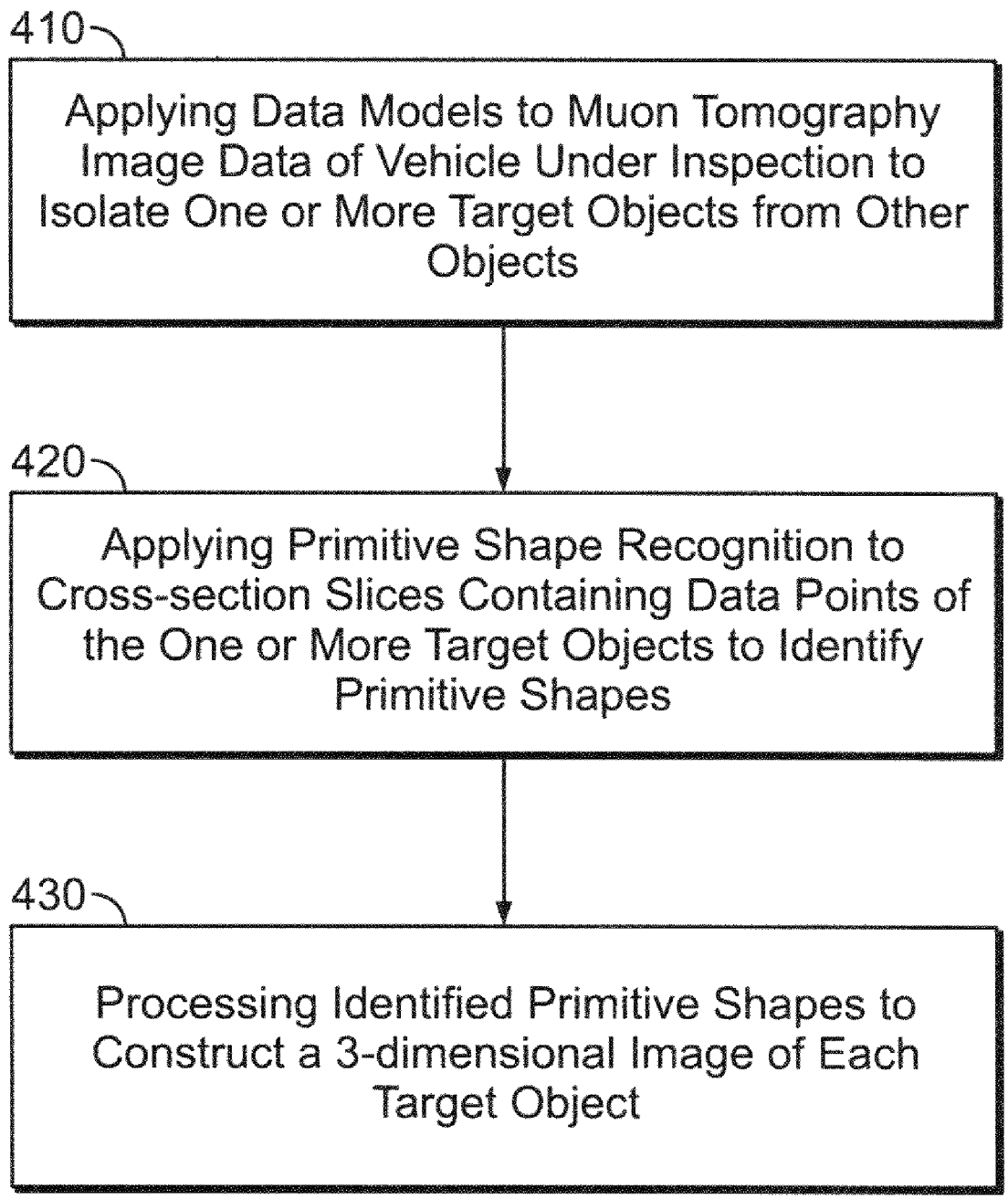
FIG. 4 shows an example of operation steps performed by the suspect object detection module in FIG. 3.

The suspect object detection module 332 is configured to include various processing modules and routes to provide a computer-automated method for processing muon vehicle imaging data based on Data Modeling. FIG. 4 shows an example of operation steps performed by the suspect object detection module 332. As illustrated, the suspect object detection module 332 applies Data Models to process muon tomography vehicle image data from the muon tomography vehicle imaging processing module 331 to isolate one or more target objects from other objects in the vehicle inspection region 130 (step 410) and subsequently applies primitive shape recognition to cross-section slices of an image of the volume 130 containing data points of the one or more target objects to identify predetermined primitive shapes (step 420). Next, the suspect object detection module 332 processes the identified primitive shapes to construct a 3-dimensional image of each target object.

The processing in step 410 can include several processing steps. First, the muon vehicle imaging data obtained from the volume 130 is processed to obtain a histogram of the muon vehicle imaging data at different positions in the volume 130 and the muon vehicle imaging data is separated into bins based on the histogram. Second, a subset of the muon vehicle imaging data in a mode bin that has higher frequencies of occurrence than remaining muon vehicle imaging data is removed from the muon vehicle imaging data to retain the remaining muon vehicle imaging data for further processing. Third, a background recognizer Data Model for identifying vehicle structures is applied to process the remaining muon vehicle imaging data to produce an image of the volume by removing the identified background structure. Subsequently, a target identification Data Model for identifying the one or more target objects is applied to process data of the image produced after applying the background recognizer Data Model to produce an image of the one or more target objects. The above processing can be performed based on the vehicle voxel data from the muon tomography vehicle imaging processing module 331 and can be achieved without relying on prior samples or data on some pre-selected known threat objects.

Figure 5:
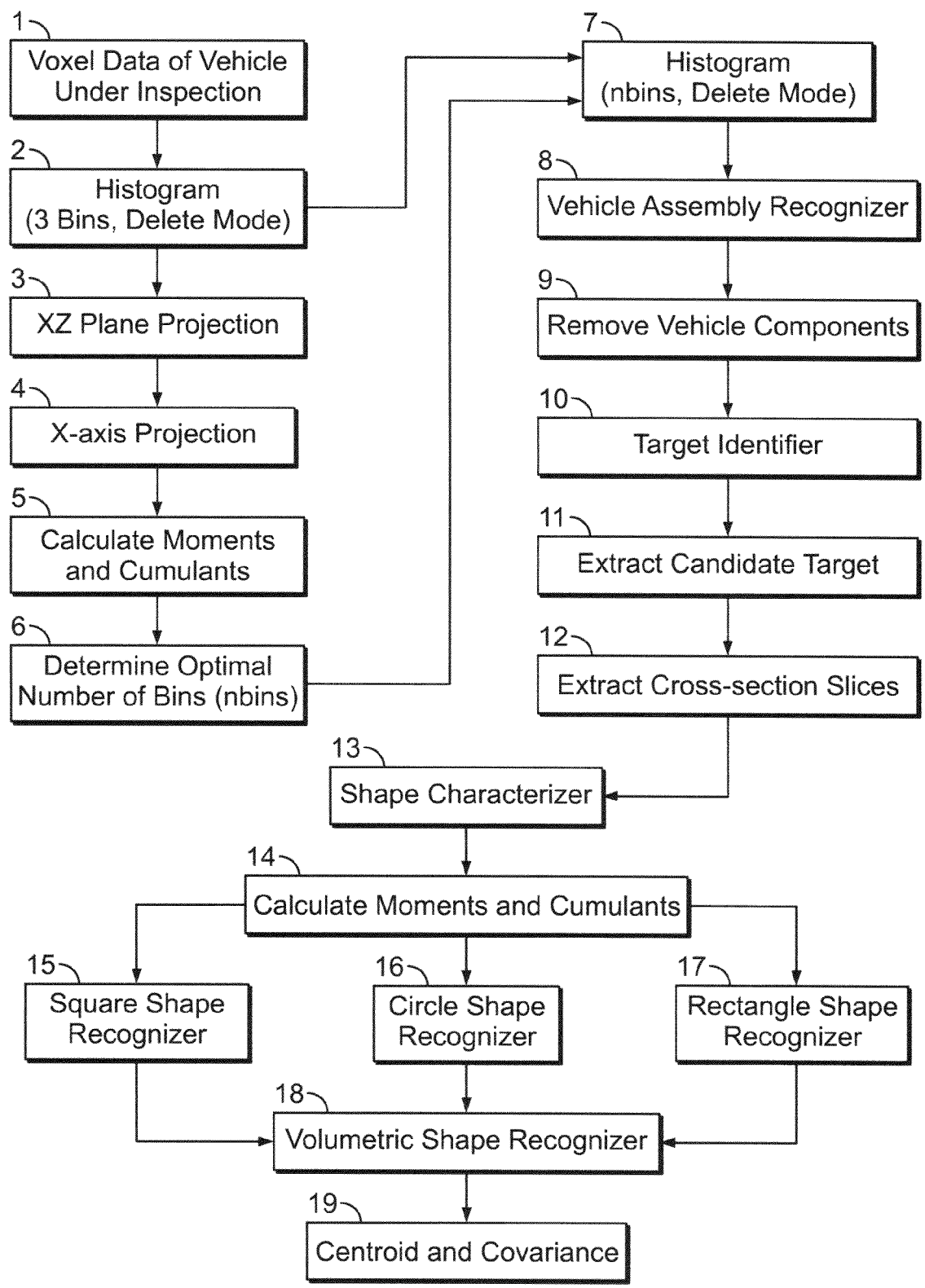
FIG. 5 shows an exemplary process that implements the processing in FIG. 4, where the Cartesian coordinates X, Y and Z are defined in FIG. 1.

FIG. 5 shows an exemplary process that implements the processing in FIG. 4. The Cartesian coordinates X, Y and Z are defined in FIG. 1. The numerals in FIG. 5 correspond the following processing steps performed by the suspect object detection module 332:

1. Receive vehicle voxel data from the muon tomography processing module 330.

2. Compute the histogram of the received vehicle voxel data and separate the histogram data into three bins. Delete data in the Mode bin which is the bin that has most frequently occurring data points or has the largest number of points. After deletion of the Mode bin, the remaining muon vehicle imaging data is used in two processing paths: (1) determination of the optimal number of bins to separate the remaining muon vehicle imaging data carried in subsequent processing steps 3-6, and (2) further processing the remaining muon vehicle imaging data to detect threat objects in subsequent processing steps 7-19.

3. Project the remaining data onto XZ plane. One of various techniques for this process is described in Jaenisch, H., Handley, J., "Data Modeling for Defense Planning", Society for Computer Simulation (Huntsville Simulation Conference 2003), Huntsville, Ala. (October, 2003).

4. Project remaining voxel rays onto the X axis.

5. Calculate moments and cumulants.

6. Determine optimal number of bins using predictive equation Data Model based on the calculated moments and cumulants. Examples of processing techniques for performing this step are described in Jaenisch, H. M. and Handley, J. W., "Data Modeling for Radar Applications", Proceedings of IEEE Radar Conference 2003; Jaenisch, H., "Enabling Unattended Data Logging and Publication by Data Model Change Detection and Environmental Awareness", SPIE Defense and Security Symposium, Orlando, Fla., April 2006; Jaenisch, H., Handley, J., Jaenisch, K., Hicklen, M., "Enabling Human HUMS with Data Modeling", SPIE Defense and Security Symposium, Orlando, Fla., April 2006; Pooley, J., Murray, S., Jaenisch, H., Handley, J., "Fault Detection via Complex Hybrid Signature Analysis", JANNAF 39th Combustion, 27th Airbreathing Propulsion, 21st Propulsion Systems Hazards, and 3rd Modeling and Simulation Subcommittees Joint Meeting, Colorado Springs, Colo., (Dec. 1-5, 2003); and Jaenisch, H., Handley, J., Hicklen, M., Vineyard, D., Ramage, M., Colthart, J., "Muon vehicle imaging and Data Modeling", Proceedings of SPIE, Defense and Security Symposium, Orlando, Fla., April 2007, Vol. 6538, No. 85.

7. Compute the histogram of the remaining data produced by the step 2 and separate the remaining data into the optimal number of bins. Once again, delete the data in the Mode bin and retain the remaining data as the target detection data for further processing.

8. Apply Vehicle Assembly Recognizer Decision equation Data Model to the remaining data produced in the step 7 to identify Z values associated with vehicle components.

9. Remove vehicle components.

10. Apply Target Medium Z Identification Decision equation Data Model to the data after removal of data associated with identified vehicle components.

11. Extract a candidate target and determine if the target exists and location of the target.

12. Extract cross-section slices.

13. Apply a shape characterizer Data Model to each extracted cross-section slice.

14. Calculate moments and cumulants of each cross-section slice.

15-17. Apply 2D primitive shape recognizer Data Models, such as a square shape recognizer Data Model, a rectangle shape recognizer Data Model, and a circle shape recognizer Data Model.

18. Perform 3D primitive shape recognition (Volumetric) using Volumetric Shape Recognizer Data Model.

19. Calculate centroids and covariances. Examples of processing techniques for performing this step are described in Jaenisch et al., "A Simple Algorithm For Sensor Fusion Using Spatial Voting (Unsupervised Object Grouping)", Proceedings of SPIE, Defense and Security Symposium 2008, Orlando, Fla., March 2008, Vol. 6968, No. 68.

Figure 6:
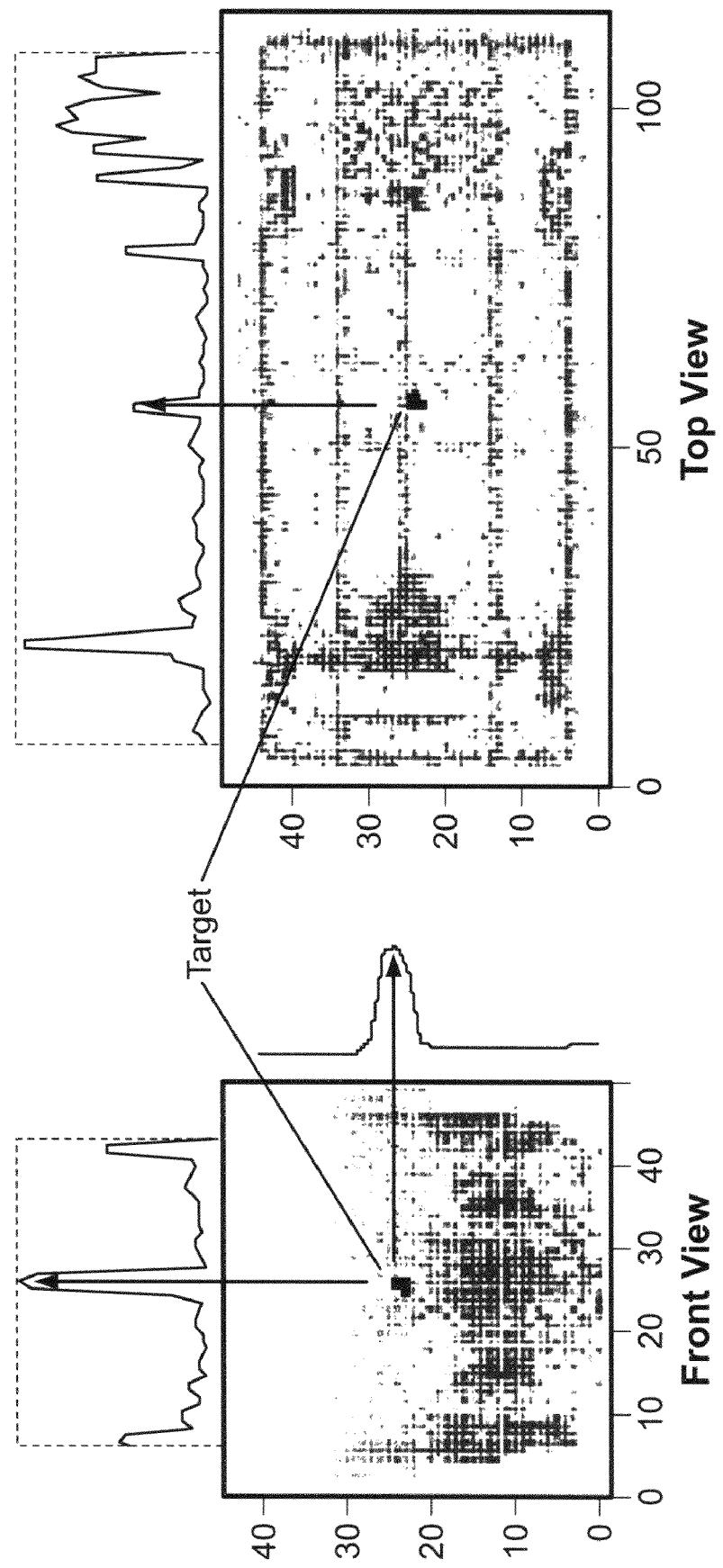
FIG. 6 shows examples of front view and top view projections of values for the characteristic data.

Once data is loaded in step 1, bulk filtering of the vehicle shell is performed by calculating a histogram using 3 bins in step 2. The mode bin (one most frequently occurring, or the one with the largest number of points) is removed in step 2, and the remainder of the (x,y,z) locations projected onto the XZ plane in step 3. The values in the XZ plane are then projected onto the X-axis of the resulting data sequence graph in step 4, which is characterized by statistics in step 5 and used with a predictive bin estimating equation to determine optimal number of bins in step 6. FIG. 6 shows examples of front view and top view projections of values for the training data.

After the optimal number of bins is determined at step 6, a histogram for the remaining data produced by the step 2 is calculated using the optimal number of bins and the data in the new Mode bin is once again deleted (step 7). The remaining points are processed through the Vehicle Assembly Recognizer Decision equation (using x, y, and z locations along with value) in step 8, and the vehicle components identified are removed in step 9. The remaining points are processed through the Target Identification Decision equation (also using x, y, and z location along with value at each point) in 10. Steps 8 and 10 isolate the candidate target which is extracted in step 11.

Figure 7A:
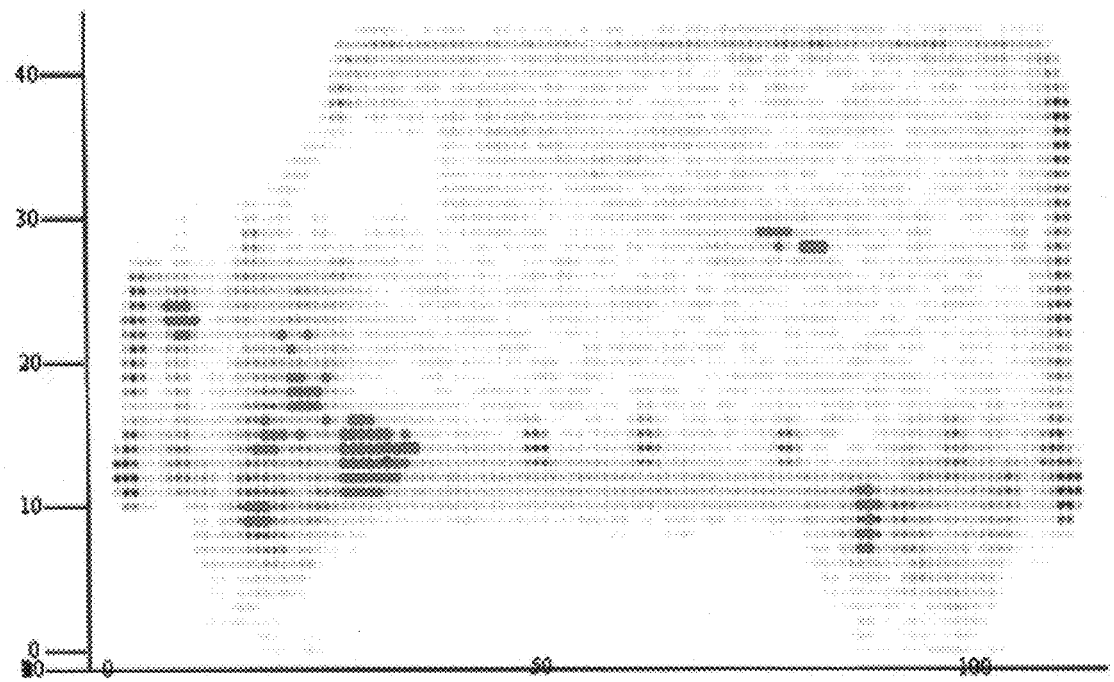
FIGS. 7A, 7B, 7C and 7D show an example for data processing based on the Vehicle Assembly Recognizer Target Identification in FIG. 5.
Figure 7B:
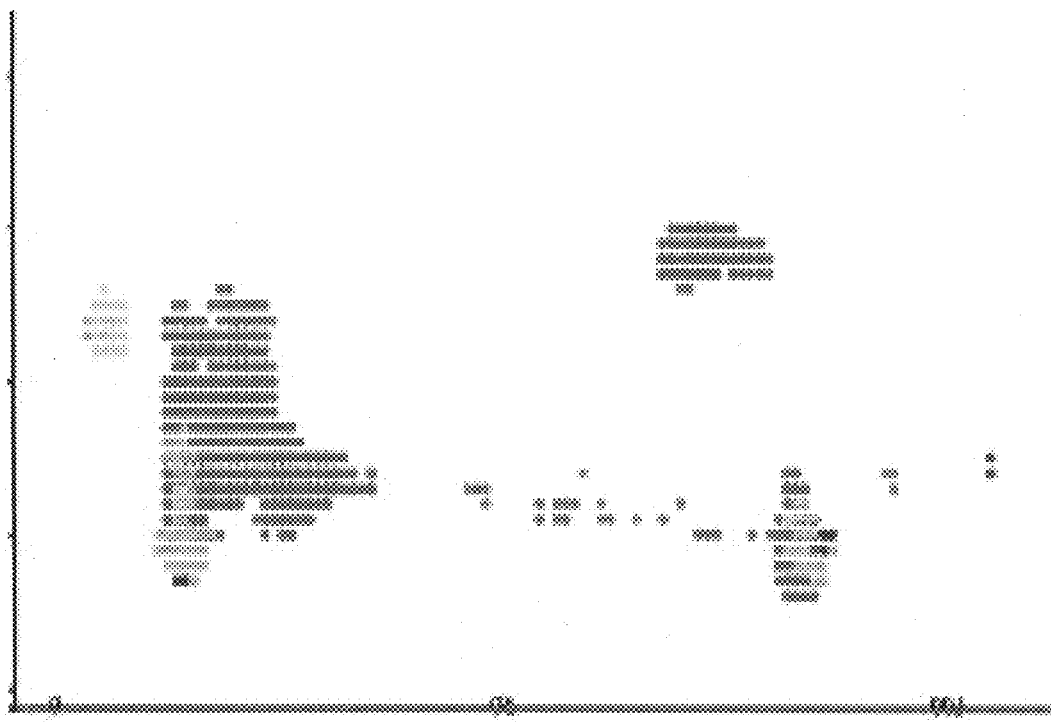
Figure 7C:
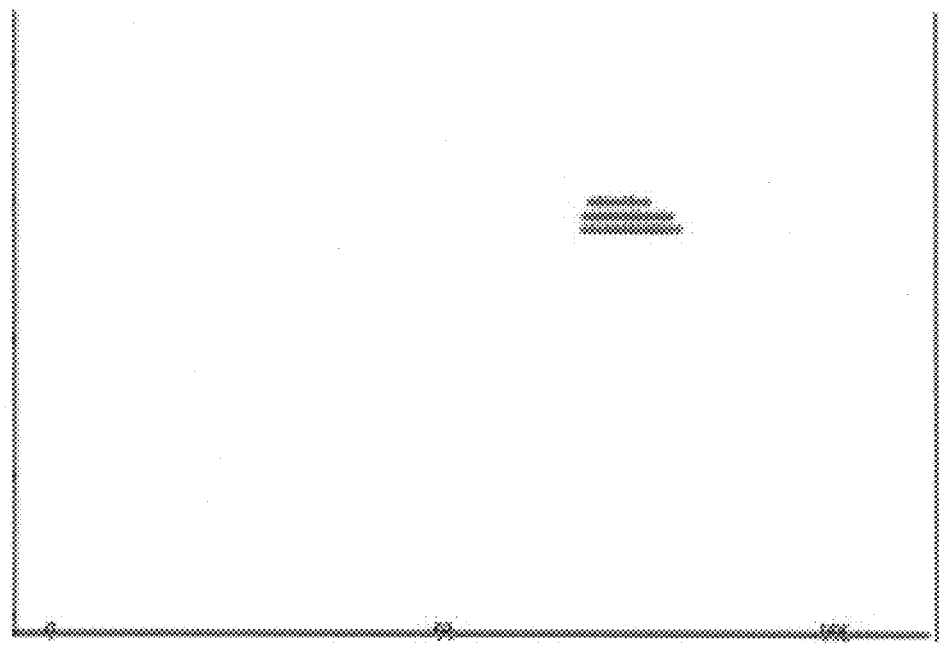
Figure 7D:
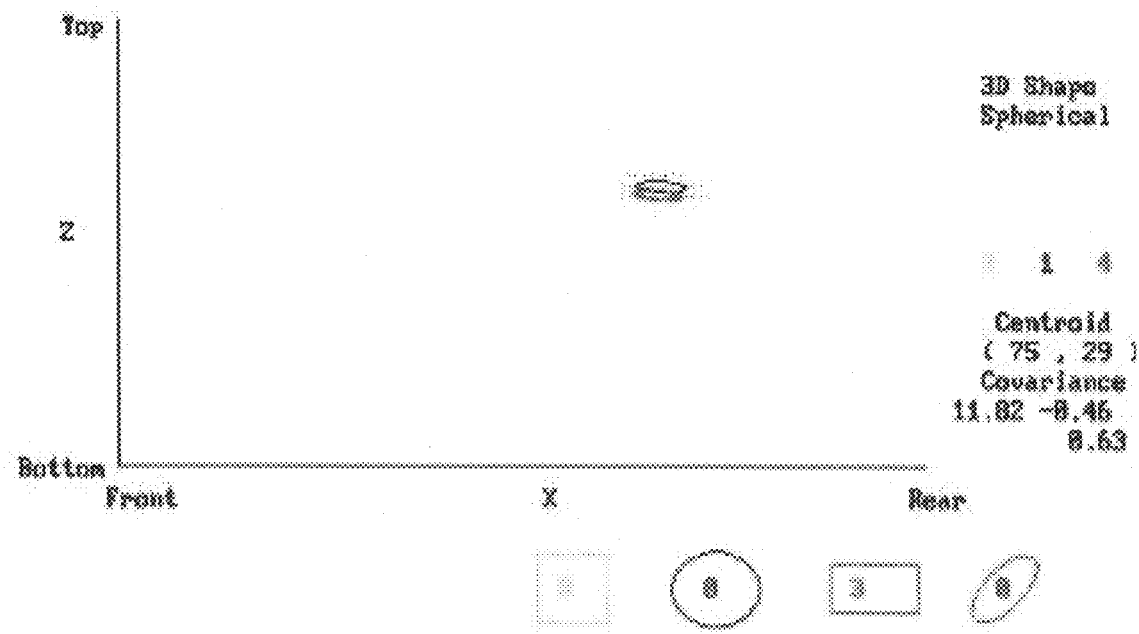

FIGS. 7A, 7B, 7C and 7D show an example for the above processing based on the Vehicle Assembly Recognizer Decision equation Target Identification Decision equation. FIG. 7A shows the projection of van data onto the XZ plane. FIG. 7B shows the XZ projection of data remaining after histogram. FIG. 7C shows the data after using Vehicle Assembly and Target Identification Data Models, respectively. The points remaining in FIG. 7C are for the potential target. FIG. 7D shows a graph of covariance ellipses for each cross-section neighborhood extracted and processed.

The above described vehicle assembly recognizer Data Model is a specific example of a background recognizer Data Model that identifies and recognizes background structure in the muon tomography data images.

Figure 8A:
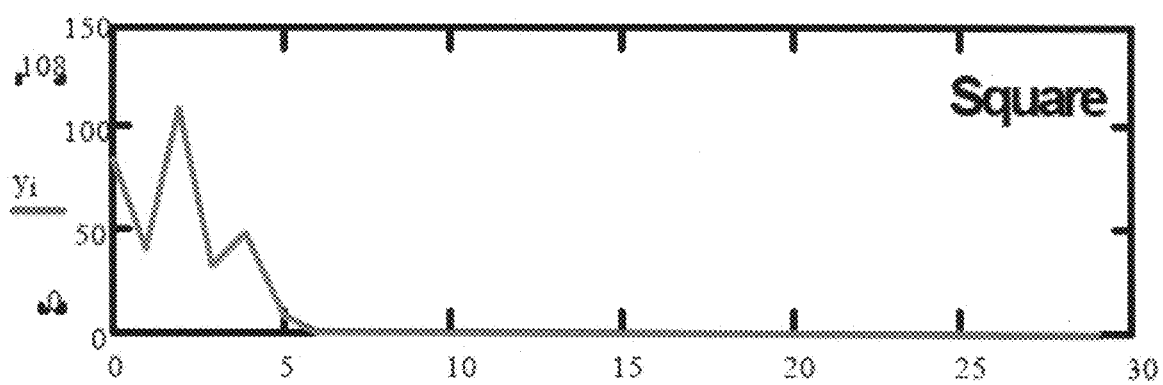
FIGS. 8A, 8B and 8C show Hamming distance curves for a square, circle, and rectangle primitive shapes in the processing in FIG. 5.
Figure 8B:
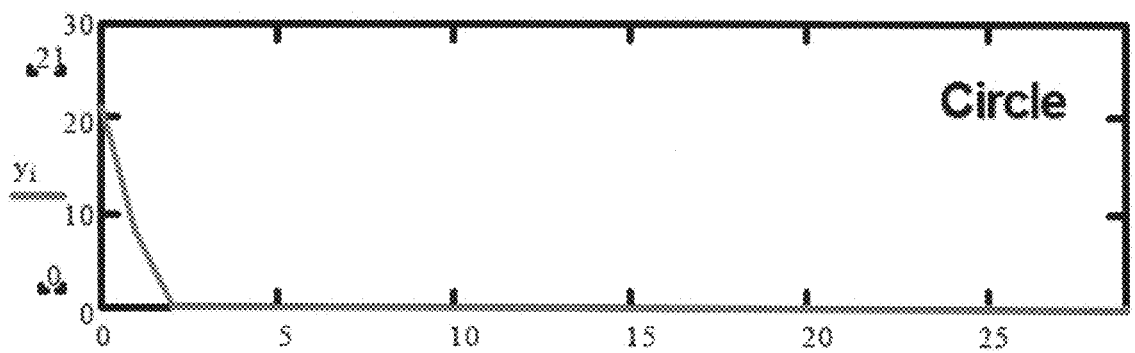
Figure 8C:
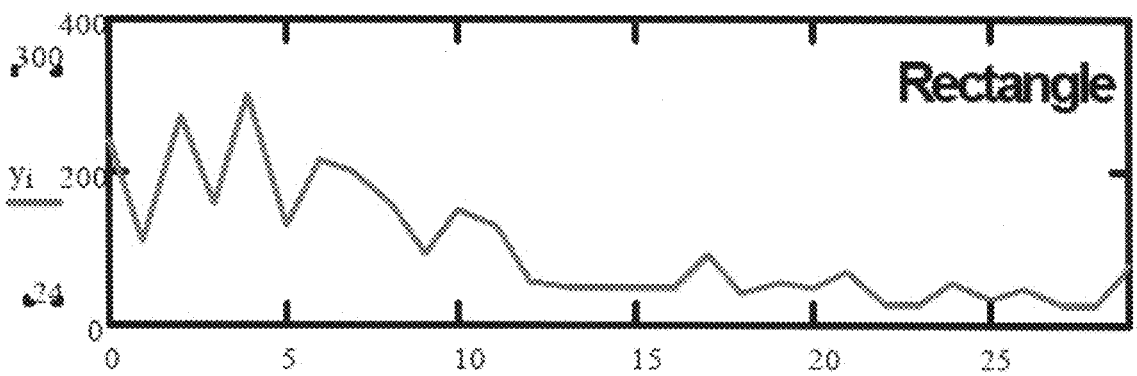

Beginning next in step 12, 2-D primitive shape detection and 3-D overall shape detection are performed. This process begins by extracting all planes, i.e., XY, XZ, and YZ slices that contain one or more of the points. These planes or slices are processed without replacement to extract all 32×32 pixel neighborhoods that contain at least one point. The shape of each neighborhood is characterized by applying the Shape Characterizer in step 13. The resulting sequence is then characterized using descriptive moments and cumulants in step 14 for input into the Shape Recognizers in steps 15, 16, and 17. In this regard, the number of pixel values in the neighborhood that change between iterations is calculated and stored as a data sequence known as the Hamming distance curves as shown in FIGS. 8A, 8B and 8C for the Square, Circle, and Rectangle Shapes. The Hamming sequence is then characterized using statistics. The statistics drive each of the Square, Circle, and Rectangle Shape Recognizers, respectively.

Upon completion of processing all of the neighborhoods, the ratio of neighborhoods flagged as square, circle, or rectangle to the total number of extracted neighborhoods is determined. FIG. 9 shows an example for this data processing to indicate the corresponding primitive shapes. If a neighborhood does not flag as any of the 3 primitive shapes, it is labeled as unrecognized. Subsequently, the Volumetric Shape Recognizer in step 18 uses the ratio of squares, circles, and rectangles flagged to total number of neighborhoods as input to determine the overall shape. Possible classifications of volumetric shape are shell, cylindrical object, elongated box, spherical, and unrecognized (possibly multiple objects). For each neighborhood extracted initially, the centroid and covariance are calculated and shown as ellipses, along with the centroid and covariance of the composite in step 19.

In one exemplary implementation of the process in FIG. 5, the following specific processing routines can be used to implement the 19 operations shown in FIG. 5.

```
1. Start with Vehicle voxel data
write(6, *)'Input File Name => '
read(5, *)pt1
open(1,file=pt1,status='unknown')
read(1, *)ix,iy,iz
allocate (YY1(0:ix*iy*iz-1,0:3))
write(6, *)'Axis lengths ',ix,iy,iz
m=0
do k=0,iz-1
   do j=0,iy-1
      do i=0,ix-1
         YY1(m,0)=i
         YY1(m,1)=j
         YY1(m,2)=k
         read(1, *)YY1(m,3)
         m=m+1
      enddo
   enddo
enddo
close(1)
2. Histogram data into 3 bins, delete Mode
call calchist(YY1,m,3,zzz,n)
subroutine calchist(Y,m,nbin,E,p)
implicit none
integer nbin,m,i,j,maxbin,maxbval,n,p
real minD, maxD, rngD, minbinD
real maxbinD, meanA, stdevA
real histt(0:nbin-1)
real D(0:m-1),E(0:m-1,0:3)
real Y(0:m-1,0:3),A(0:m-1)
minD=Y(0,3)
maxD=Y(0,3)
do i=0, m-1
   D(i)=Y(i,3)
   if(D(i).gt.maxD)maxD=D(i)
   if(D(i).lt.minD)minD=D(i)
enddo
rngD=maxD-minD
```

```
      do i=0,nbin−1
         histt(i)=0
      enddo
      do i=0,m−1
         do j=0,nbin−1
            if(D(i).ge.(minD+j*rngD/nbin) .and. D(i).lt.
   +           (minD + (j + 1)*rngD/nbin))histt(j)=histt(j)+1
         enddo
      enddo
      maxbin=0
      maxbval=histt(0)
      do j=1,nbin−1
         if(histt(j).ge.maxbval) then
            maxbin=j
            maxbval=histt(j)
         endif
      enddo
      minbinD=minD+maxbin*rngD/nbin
      maxbinD=minD+(maxbin+1)*rngD/nbin
      A(0)=0
      n=0
      p=0
      do i=0,m−1
         if(D(i).ge.minbinD .and. D(i).le.maxbinD) then
            A(n)=D(i)
            n=n + 1
         else
            do j=0,3
               E(p,j)=Y(i,j)
            enddo
            p=p+1
         endif
      enddo
      call mean(A,n,meanA)
      call stdev(A,n,stdevA)
      do i=0,p−1
         E(i,3)=(E(i,3)−meanA)/stdevA
      enddo
      return
      end
3. Project remaining data onto XZ plane
      subroutine extractplanes(X,Y,Z,A,ix,iy,iz,B,n1,n2,n3,n)
      implicit none
      integer ix,iy,iz,n1,n2,n3,i,j,k,n
      integer X(0:n−1),Y(0:n−1),Z(0:n−1),A(0:ix−1,0:iy−1,0:iz−1)
      integer B(0:n1+n2+n3−1, 0:ix−1, 0:ix−1)
      write(6, *)n1,n2,n3
      do i=0,n1−1
         do j=0,iy−1
            do k=0,iz−1
               B(i,j,k)=A(X(i),j,k)
            enddo
         enddo
      enddo
      do i=0,n2−1
         do j=0,ix−1
            do k=0,iz−1
               B(n1+i,j,k)=A(j,Y(i),k)
            enddo
         enddo
      enddo
      do i=0,n3−1
         do j=0,ix−1
            do k=0,iy−1
               B(n1+n2+i,j,k)=A(j,k,Z(i))
            enddo
         enddo
      enddo
      return
      end
4. Project remaining voxel rays onto X axis (included in code for step 3)
5. Calculate Moments and Cumulants.
      subroutine mean(A,n,meanA)
      implicit none
      integer n,i
      real A(0:n−1)
      real meanA
      meanA=0.0
      do i=0,n−1
         meanA=meanA+A(i)/n
```

```
    enddo
    return
    end
subroutine stdev(A,n,stdevA)
    implicit none
    integer n,i
    real A(0:n-1)
    real stdevA,meanA,s,pp
    stdevA=0.0
    meanA=0.0
    do i=0,n-1
        meanA=meanA+A(i)/n
    enddo
    do i=0,n-1
        s=A(i)-meanA
        pp=s*s
        stdevA=stdevA+pp
    enddo
    stdevA=sqrt(stdevA/(n-1))
    return
    end
subroutine skewness(A,n,ystat)
    implicit none
    integer n
    real A(0:n-1)
    integer i
    real ystat,ymean,ystdev
    call mean(A,n,ymean)
    call stdev(A,n,ystdev)
    ystat=0
    do i=0,n-1
        ystat=ystat+(1/n)*((A(i)-ymean)/ystdev)**3
    enddo
    return
    end
subroutine kurtosis(A,n,ystat)
    implicit none
    integer n
    real A(0:n-1)
    integer i
    real ystat,ymean,ystdev
    call mean(A,n,ymean)
    call stdev(A,n,ystdev)
    ystat=0
    do i=0,n-1
        ystat=ystat+(1/n)*((A(i)-ymean)/ystdev)**4
    enddo
    ystat=ystat-3
    return
    end
```

6. Determine optimal number of bins using predictive equation Data Model

```
cls
on error resume next
input "stdev => ", stdev
avg0=0
dev0=1
stdev =(stdev - avg0) / dev0
input "skew => ", skew
avg1=0
dev1=1
skew = (skew - avg1) / dev1
input "kurt => ", kurt
avg2=0
dev2=1
kurt = (kurt - avg2) / dev2
t1 = 3996.8959
t1=t1 + -2034.3165*stdev
t1=t1 + -7531.7086*skew
t1=t1 + 1462.2043*kurt
t1=t1 + 406.1663*stdev*stdev
t1=t1 + 4485.9879*skew*skew
t1=t1 + 144.8136*kurt*kurt
t1=t1 + 2368.6092*stdev*skew
t1=t1 + -433.4313*stdev*kurt
t1=t1 + -1658.6568*skew*kurt
t1=t1 + 210.6329*stdev*skew*kurt
t1=t1 + -17.9517*stdev*stdev*stdev
t1=t1 + -883.0253*skew*skew*skew
t1=t1 + 4.7155*kurt*kurt*kurt
t1=t1 + -261.7948*skew*stdev*stdev
```

-continued

```
t1=t1 + −612.5371*stdev*skew*skew
t1=t1 + −16.8366*stdev*kurt*kurt
t1=t1 + 46.8615*kurt*stdev*stdev
t1=t1 + 477.7376*kurt*skew*skew
t1=t1 + −83.0172*skew*kurt*kurt
t2 = −962.0357
t2=t2 + 934.7015*stdev
t2=t2 + 602.9623*skew
t2=t2 + −333.8504*stdev*stdev
t2=t2 + −133.4822*skew*skew
t2=t2 + −349.8407*stdev*skew
t2=t2 + 44.3898*stdev*stdev*stdev
t2=t2 + 9.9078*skew*skew*skew
t2=t2 + 52.4919*skew*stdev*stdev
t2=t2 + 38.1055*stdev*skew*skew
t3 = −251.5042
t3=t3 + 402.1001*stdev
t3=t3 + 33.9866*kurt
t3=t3 + −212.6009*stdev*stdev
t3=t3 + −1.804*kurt*kurt
t3=t3 + −31.4003*stdev*kurt
t3=t3 + 37.3747*stdev*stdev*stdev
t3=t3 + 0.031*kurt*kurt*kurt
t3=t3 + 7.362*kurt*stdev*stdev
t3=t3 + 0.8384*stdev*kurt*kurt
t4 = −150.1537
t4=t4 + −31.6181*t1
t4=t4 + 287.8003*stdev
t4=t4 + 57.6673*t2
t4=t4 + −0.773*t1*t1
t4=t4 + −190.0648*stdev*stdev
t4=t4 + −11.2456*t2*t2
t4=t4 + −0.1633*t1*stdev
t4=t4 + 9.6926*t1*t2
t4=t4 + −21.4703*stdev*t2
t4=t4 + 2.656*t1*stdev*t2
t4=t4 + −0.077*t1*t1*t1
t4=t4 + 41.7226*stdev*stdev*stdev
t4=t4 + 0.9628*t2*t2*t2
t4=t4 + −1.5302*stdev*t1*t1
t4=t4 + 2.237*t1*stdev*stdev
t4=t4 + −1.4072*t1*t2*t2
t4=t4 + 0.5811*t2*t1*t1
t4=t4 + 2.7992*t2*stdev*stdev
t4=t4 + −0.1588*stdev*t2*t2
t5 = −22.5943
t5=t5 + −18.4502*t1
t5=t5 + 35.9303*t2
t5=t5 + −6.8155*t3
t5=t5 + −2.2486*t1*t1
t5=t5 + 51.4807*t2*t2
t5=t5 + 24.0612*t3*t3
t5=t5 + −29.7499*t1*t2
t5=t5 + 39.3189*t1*t3
t5=t5 + −84.1592*t2*t3
t5=t5 + 21.6412*t1*t2*t3
t5=t5 + 0.0136*t1*t1*t1
t5=t5 + 5.3467*t2*t2*t2
t5=t5 + 0.4352*t3*t3*t3
t5=t5 + 2.353*t2*t1*t1
t5=t5 + −11.1333*t1*t2*t2
t5=t5 + −11.3915*t1*t3*t3
t5=t5 + −2.089*t3*t1*t1
t5=t5 + −11.921*t3*t2*t2
t5=t5 + 6.8004*t2*t3*t3
t6 = −35.6965
t6=t6 + −34.3335*t1
t6=t6 + 8.3038*stdev
t6=t6 + 50.8947*t3
t6=t6 + −0.4694*t1*t1
t6=t6 + −3.7115*stdev*stdev
t6=t6 + −9.7482*t3*t3
t6=t6 + 9.4526*t1*stdev
t6=t6 + 8.0349*t1*t3
t6=t6 + −10.3683*stdev*t3
t6=t6 + −0.6248*t1*stdev*t3
t6=t6 + 0.033*t1*t1*t1
t6=t6 + 4.4541*stdev*stdev*stdev
t6=t6 + 0.5147*t3*t3*t3
t6=t6 + −0.2535*stdev*t1*t1
```

```
t6=t6 + 0.6433*t1*stdev*stdev
t6=t6 + -0.5219*t1*t3*t3
t6=t6 + 0.0365*t3*t1*t1
t6=t6 + -3.4256*t3*stdev*stdev
t6=t6 + 1.502*stdev*t3*t3
t7 = 3.821
t7=t7 + -2.6472*t4
t7=t7 + 4.7821*t5
t7=t7 + -2.8123*t6
t7=t7 + -2.8771*t4*t4
t7=t7 + -5.9143*t5*t5
t7=t7 + 0.8615*t6*t6
t7=t7 + 8.755*t4*t5
t7=t7 + -2.6803*t4*t6
t7=t7 + 2.0996*t5*t6
t7=t7 + 1.951*t4*t5*t6
t7=t7 + 1.674*t4*t4*t4
t7=t7 + 0.1775*t5*t5*t5
t7=t7 + -0.4787*t6*t6*t6
t7=t7 + -3.9432*t5*t4*t4
t7=t7 + 2.5218*t4*t5*t5
t7=t7 + 0.1642*t4*t6*t6
t7=t7 + -0.8945*t6*t4*t4
t7=t7 + -2.3395*t6*t5*t5
t7=t7 + 1.1562*t5*t6*t6
t8 = -2.2118
t8=t8 + 3.9246*t4
t8=t8 + 29.6485*stdev
t8=t8 + -4.3768*t5
t8=t8 + -5.1916*t4*t4
t8=t8 + -24.7618*stdev*stdev
t8=t8 + -6.6462*t5*t5
t8=t8 + -18.2263*t4*stdev
t8=t8 + 12.1779*t4*t5
t8=t8 + 15.0158*stdev*t5
t8=t8 + -2.1248*t4*stdev*t5
t8=t8 + 0.895*t4*t4*t4
t8=t8 + 5.6838*stdev*stdev*stdev
t8=t8 + -0.4061*t5*t5*t5
t8=t8 + 1.0503*stdev*t4*t4
t8=t8 + 7.1515*t4*stdev*stdev
t8=t8 + 1.7875*t4*t5*t5
t8=t8 + -2.293*t5*t4*t4
t8=t8 + -5.6934*t5*stdev*stdev
t8=t8 + 1.1406*stdev*t5*t5
nbins = 251.4737
nbins=nbins + 49.4576*t7
nbins=nbins + -422.8133*stdev
nbins=nbins + -79.0417*t8
nbins=nbins + 2.6774*t7*t7
nbins=nbins + 224.8445*stdev*stdev
nbins=nbins + 10.196*t8*t8
nbins=nbins + -33.2568*t7*stdev
nbins=nbins + -11.5861*t7*t8
nbins=nbins + 67.0927*stdev*t8
nbins=nbins + 7.0562*t7*stdev*t8
nbins=nbins + 0.5882*t7*t7*t7
nbins=nbins + -38.7188*stdev*stdev*stdev
nbins=nbins + -0.8134*t8*t8*t8
nbins=nbins + -2.2341*stdev*t7*t7
nbins=nbins + 4.2043*t7*stdev*stdev
nbins=nbins + 2.0341*t7*t8*t8
nbins=nbins + -1.823*t8*t7*t7
nbins=nbins + -12.6836*t8*stdev*stdev
nbins=nbins + -5.6006*stdev*t8*t8
nbins = int(nbins)
print "nbins = ", format$(nbins,"0.000000")
end
   7. Bin Data using optimal number of bins and Delete Mode
   call calchist(YY1,m,nbins,zzz,n)
   subroutine calchist(Y,m,nbin,E,p)
   implicit none
   integer nbin,m,i,j,maxbin,maxbval,n,p
   real minD,maxD,rngD,minbinD,maxbinD,meanA,stdevA
   real histt(0:nbin-1)
   real D(0:m-1),E(0:m-1,0:3),Y(0:m-1,0:3),A(0:m-1)
   minD=Y(0,3)
   maxD=Y(0,3)
   do i=0, m-1
      D(i)=Y(i,3)
```

```
        if(D(i).gt.maxD)maxD=D(i)
        if(D(i).lt.minD)minD=D(i)
    enddo
    rngD=maxD-minD
    do i=0,nbin-1
        histt(i)=0
    enddo
    do i=0,m-1
        do j=0,nbin-1
            if(D(i).ge.(minD+j*rngD/nbin) .and. D(i).lt.
   +            (minD+(j+1)*rngD/nbin))histt(j)=histt(j)+1
        enddo
    enddo
    maxbin=0
    maxbval=histt(0)
    doj=1,nbin-1
        if(histt(j).ge.maxbval) then
            maxbin=j
            maxbval=histt(j)
        endif
    enddo
    minbinD=minD+maxbin*rngD/nbin
    maxbinD=minD+(maxbin+1)*rngD/nbin
    A(0)=0
    n=0
    p=0
    do i=0,m-1
        if(D(i).ge.minbinD .and. D(i).le.maxbinD) then
            A(n)=D(i)
            n=n+1
        else
            do j=0,3
                E(p,j)=Y(i,j)
            enddo
            p=p+1
        endif
    enddo
    call mean(A,n,meanA)
    call stdev(A,n,stdevA)
    do i=0,p-1
        E(i,3) =(E(i,3)-meanA)/stdevA
    enddo
    return
    end
8. Apply Vehicle Assembly Recognizer Decision equation Data Model
cls
on error resume next
input "xloc => ", xloc
avg0=28.8234
dev0=16.2348
xloc =(xloc - avg0) / dev0
input "yloc => ", yloc
avg1=24.7133
dev1=5.1657
yloc = (yloc - avg1) / dev1
input "zloc => ", zloc
avg2=15.1265
dev2=4.2319
zloc = (zloc - avg2) / dev2
input "zval => ", zval
avg3=28.9563
dev3=12.9545
zval = (zval - avg3) / dev3
t1 = 0.1
t1=t1 + -0.1508*xloc
t1=t1 + -0.1539*yloc
t1=t1 + 1.1732*zloc
t1=t1 + -0.0228*xloc*xloc
t1=t1 + 0.0079*yloc*yloc
t1=t1 + -0.0833*zloc*zloc
t1=t1 + -0.1833*xloc*yloc
t1=t1 + -0.1095*xloc*zloc
t1=t1 + 0.0294*yloc*zloc
t1=t1 + -0.0265*xloc*yloc*zloc
t1=t1 + 0.0165*xloc*xloc*xloc
t1=t1 + 0.0046*yloc*yloc*yloc
t1=t1 + -0.1393*zloc*zloc*zloc
t1=t1 + 0.0516*yloc*xloc*xloc
t1=t1 + -0.0016*xloc*yloc*yloc
t1=t1 + 0.0422*xloc*zloc*zloc
```

```
t1=t1 + 0.0464*zloc*xloc*xloc
t1=t1 + −0.0008*zloc*yloc*yloc
t1=t1 + 0.0074*yloc*zloc*zloc
t2 = 0.1147
t2=t2 + 0.0036*yloc
t2=t2 + 1.2614*zloc
t2=t2 + 0.0105*zval
t2=t2 + 0.0363*yloc*yloc
t2=t2 + −0.0721*zloc*zloc
t2=t2 + −0.0023*zval*zval
t2=t2 + 0.0742*yloc*zloc
t2=t2 + 0.0309*yloc*zval
t2=t2 + −0.0188*zloc*zval
t2=t2 + 0.0129*yloc*zloc*zval
t2=t2 + 0.0088*yloc*yloc*yloc
t2=t2 + −0.159*zloc*zloc*zloc
t2=t2 + 0.0004*zval*zval*zval
t2=t2 + 0.0237*zloc*yloc*yloc
t2=t2 + 0.0145*yloc*zloc*zloc
t2=t2 + −0.0056*yloc*zval*zval
t2=t2 + 0.0007*zval*yloc*yloc
t2=t2 + −0.0143*zval*zloc*zloc
t2=t2 + 0.0071*zloc*zval*zval
vehicreg = −0.0902
vehicreg=vehicreg + 1.1065*t1
vehicreg=vehicreg + −1.4047*zloc
vehicreg=vehicreg + 1.267*t2
vehicreg=vehicreg + −0.1239*t1*t1
vehicreg=vehicreg + −0.3097*zloc*zloc
vehicreg=vehicreg + −1.7494*t2*t2
vehicreg=vehicreg + −0.6863*t1*zloc
vehicreg=vehicreg + 1.35*t1*t2
vehicreg=vehicreg + 1.5229*zloc*t2
vehicreg=vehicreg + −0.4454*t1*zloc*t2
vehicreg=vehicreg + −2.1904*t1*t1*t1
vehicreg=vehicreg + 0.3772*zloc*zloc*zloc
vehicreg=vehicreg + 3.0995*t2*t2*t2
vehicreg=vehicreg + 0.6835*zloc*t1*t1
vehicreg=vehicreg + −0.0339*t1*zloc*zloc
vehicreg=vehicreg + −7.117*t1*t2*t2
vehicreg=vehicreg + 6.3359*t2*t1*t1
vehicreg=vehicreg + −0.2997*t2*zloc*zloc
vehicreg=vehicreg + −0.4166*zloc*t2*t2
vehicreg=vehicreg*0.8427 + 2.1317
print "vehicreg = ", format$(vehicreg, "0.000000")
end
9. Remove Vehicle Components
do i=0,n−1
   zj1(i)=real(nint(zj1(i)))
   if (zj1(i).lt.0 .or. zj1(i).gt.5)then
      zj1(i)=1
   else
      zj1(i)=0
   end if
enddo
10. Apply Target Medium Z Identification Decision equation Data Model
cls
on error resume next
input "xloc => ", xloc
avg0=28.8234
dev0=16.2348
xloc = (xloc − avg0) / dev0
input "yloc => ", yloc
avg1=24.7133
dev1=5.1657
yloc = (yloc − avg1) / dev1
input "zloc => ", zloc
avg2=15.1265
dev2=4.2319
zloc = (zloc − avg2) / dev2
input "zval => ", zval
avg3=28.9563
dev3=12.9545
zval = (zval − avg3) / dev3
t1 = 0.1
t1=t1 + −0.1508*xloc
t1=t1 + −0.1539*yloc
t1=t1 + 1.1732*zloc
t1=t1 + −0.0228*xloc*xloc
t1=t1 + 0.0079*yloc*yloc
```

```
t1=t1 + −0.0833*zloc*zloc
t1=t1 + −0.1833*xloc*yloc
t1=t1 + −0.1095*xloc*zloc
t1=t1 + 0.0294*yloc*zloc
t1=t1 + −0.0265*xloc*yloc*zloc
t1=t1 + 0.0165*xloc*xloc*xloc
t1=t1 + 0.0046*yloc*yloc*yloc
t1=t1 + −0.1393*zloc*zloc*zloc
t1=t1 + 0.0516*yloc*xloc*xloc
t1=t1 + −0.0016*xloc*yloc*yloc
t1=t1 + 0.0422*xloc*zloc*zloc
t1=t1 + 0.0464*zloc*xloc*xloc
t1=t1 + −0.0008*zloc*yloc*yloc
t1=t1 + 0.0074*yloc*zloc*zloc
t2 = 0.032
t2=t2 + −0.2285*xloc
t2=t2 + 1.0758*zloc
t2=t2 + 0.0218*zval
t2=t2 + 0.0643*xloc*xloc
t2=t2 + −0.0616*zloc*zloc
t2=t2 + −0.0043*zval*zval
t2=t2 + −0.2528*xloc*zloc
t2=t2 + −0.0196*xloc*zval
t2=t2 + −0.0048*zloc*zval
t2=t2 + −0.0193*xloc*zloc*zval
t2=t2 + 0.0001*xloc*xloc*xloc
t2=t2 + −0.1435*zloc*zloc*zloc
t2=t2 + 0.0005*zval*zval*zval
t2=t2 + 0.0996*zloc*xloc*xloc
t2=t2 + 0.0406*xloc*zloc*zloc
t2=t2 + 0.0003*xloc*zval*zval
t2=t2 + −0.001*zval*xloc*xloc
t2=t2 + −0.0125*zval*zloc*zloc
t2=t2 + 0.0036*zloc*zval*zval
t3 = 0.1147
t3=t3 + 0.0036*yloc
t3=t3 + 1.2614*zloc
t3=t3 + 0.0105*zval
t3=t3 + 0.0363*yloc*yloc
t3=t3 + −0.0721*zloc*zloc
t3=t3 + −0.0023*zval*zval
t3=t3 + 0.0742*yloc*zloc
t3=t3 + 0.0309*yloc*zval
t3=t3 + −0.0188*zloc*zval
t3=t3 + 0.0129*yloc*zloc*zval
t3=t3 + 0.0088*yloc*yloc*yloc
t3=t3 + −0.159*zloc*zloc*zloc
t3=t3 + 0.0004*zval*zval*zval
t3=t3 + 0.0237*zloc*yloc*yloc
t3=t3 + 0.0145*yloc*zloc*zloc
t3=t3 + −0.0056*yloc*zval*zval
t3=t3 + 0.0007*zval*yloc*yloc
t3=t3 + −0.0143*zval*zloc*zloc
t3=t3 + 0.0071*zloc*zval*zval
t4 = −0.0902
t4=t4 + 1.1065*t1
t4=t4 + −1.4047*zloc
t4=t4 + 1.267*t3
t4=t4 + −0.1239*t1*t1
t4=t4 + −0.3097*zloc*zloc
t4=t4 + −1.7494*t3*t3
t4=t4 + −0.6863*t1*zloc
t4=t4 + 1.35*t1*t3
t4=t4 + 1.5229*zloc*t3
t4=t4 + −0.4454*t1*zloc*t3
t4=t4 + −2.1904*t1*t1*t1
t4=t4 + 0.3772*zloc*zloc*zloc
t4=t4 + 3.0995*t3*t3*t3
t4=t4 + 0.6835*zloc*t1*t1
t4=t4 + −0.0339*t1*zloc*zloc
t4=t4 + −7.117*t1*t3*t3
t4=t4 + 6.3359*t3*t1*t1
t4=t4 + −0.2997*t3*zloc*zloc
t4=t4 + −0.4166*zloc*t3*t3
t5 = 0.1215
t5=t5 + −0.3914*t2
t5=t5 + −0.1228*xloc
t5=t5 + 1.4642*t3
t5=t5 + −2.8041*t2*t2
t5=t5 + −0.1571*xloc*xloc
```

```
t5=t5 + −2.8051*t3*t3
t5=t5 + −0.6428*t2*xloc
t5=t5 + 5.2211*t2*t3
t5=t5 + 0.0726*xloc*t3
t5=t5 + −4.1602*t2*xloc*t3
t5=t5 + 3.817*t2*t2*t2
t5=t5 + 0.034*xloc*xloc*xloc
t5=t5 + −1.3168*t3*t3*t3
t5=t5 + 1.859*xloc*t2*t2
t5=t5 + 0.3431*t2*xloc*xloc
t5=t5 + 6.6148*t2*t3*t3
t5=t5 + −9.3625*t3*t2*t2
t5=t5 + −0.4085*t3*xloc*xloc
t5=t5 + 1.8654*xloc*t3*t3
t6 = 0.0032
t6=t6 + 1.9491*t3
t6=t6 + −0.0768*xloc
t6=t6 + −0.9715*zloc
t6=t6 + −0.8872*t3*t3
t6=t6 + −0.1115*xloc*xloc
t6=t6 + −0.4895*zloc*zloc
t6=t6 + −0.2123*t3*xloc
t6=t6 + 1.2271*t3*zloc
t6=t6 + −0.119*xloc*zloc
t6=t6 + 0.019*t3*xloc*zloc
t6=t6 + 0.0383*t3*t3*t3
t6=t6 + 0.0252*xloc*xloc*xloc
t6=t6 + 0.3739*zloc*zloc*zloc
t6=t6 + −0.2305*xloc*t3*t3
t6=t6 + −0.0578*t3*xloc*xloc
t6=t6 + −0.4851*t3*zloc*zloc
t6=t6 + −0.0524*zloc*t3*t3
t6=t6 + 0.0566*zloc*xloc*xloc
t6=t6 + 0.0326*xloc*zloc*zloc
t7 = −0.0003
t7=t7 + 1.7744*t5
t7=t7 + −0.01*zloc
t7=t7 + −0.7502*t6
t7=t7 + 0.2615*t5*t5
t7=t7 + −0.2461*zloc*zloc
t7=t7 + −0.4588*t6*t6
t7=t7 + −0.2182*t5*zloc
t7=t7 + −0.0551*t5*t6
t7=t7 + 0.7274*zloc*t6
t7=t7 + 3.2643*t5*zloc*t6
t7=t7 + −2.9004*t5*t5*t5
t7=t7 + 0.2584*zloc*zloc*zloc
t7=t7 + 4.5188*t6*t6*t6
t7=t7 + −1.9513*zloc*t5*t5
t7=t7 + −0.0356*t5*zloc*zloc
t7=t7 + −12.5793*t5*t6*t6
t7=t7 + 10.8537*t6*t5*t5
t7=t7 + −0.6884*t6*zloc*zloc
t7=t7 + −0.7478*zloc*t6*t6
t8 = 0.0086
t8=t8 + 0.221*t4
t8=t8 + −0.0715*zloc
t8=t8 + 0.84*t5
t8=t8 + −0.2009*t4*t4
t8=t8 + −0.234*zloc*zloc
t8=t8 + 0.1087*t5*t5
t8=t8 + 0.5239*t4*zloc
t8=t8 + −0.1962*t4*t5
t8=t8 + −0.0019*zloc*t5
t8=t8 + 1.0789*t4*zloc*t5
t8=t8 + 1.6506*t4*t4*t4
t8=t8 + 0.1764*zloc*zloc*zloc
t8=t8 + −1.0135*t5*t5*t5
t8=t8 + −0.0216*zloc*t4*t4
t8=t8 + −0.4746*t4*zloc*zloc
t8=t8 + 4.2787*t4*t5*t5
t8=t8 + −4.8714*t5*t4*t4
t8=t8 + 0.0866*t5*zloc*zloc
t8=t8 + −0.8898*zloc*t5*t5
t9 = 0.03
t9=t9 + 0.3106*t4
t9=t9 + 0.0331*xloc
t9=t9 + 0.6825*t5
t9=t9 + 0.6573*t4*t4
t9=t9 + −0.0117*xloc*xloc
```

```
t9=t9 + 0.4201*t5*t5
t9=t9 + 0.3835*t4*xloc
t9=t9 + −1.1068*t4*t5
t9=t9 + −0.36*xloc*t5
t9=t9 + 0.6052*t4*xloc*t5
t9=t9 + 0.4543*t4*t4*t4
t9=t9 + −0.0001*xloc*xloc*xloc
t9=t9 + −0.7816*t5*t5*t5
t9=t9 + −0.3329*xloc*t4*t4
t9=t9 + −0.0653*t4*xloc*xloc
t9=t9 + 2.0233*t4*t5*t5
t9=t9 + −1.6749*t5*t4*t4
t9=t9 + 0.0428*t5*xloc*xloc
t9=t9 + −0.2963*xloc*t5*t5
targid = −0.0028
targid=targid + 0.9135*t7
targid=targid + 0.1295*t8
targid=targid + −0.0366*t9
targid=targid + 0.4651*t7*t7
targid=targid + −3.707*t8*t8
targid=targid + 1.377*t9*t9
targid=targid + 4.4745*t7*t8
targid=targid + −5.0282*t7*t9
targid=targid + 2.4147*t8*t9
targid=targid + 69.3333*t7*t8*t9
targid=targid + −1.2669*t7*t7*t7
targid=targid + 31.8732*t8*t8*t8
targid=targid + 1.0329*t9*t9*t9
targid=targid + 1.0146*t8*t7*t7
targid=targid + −34.6345*t7*t8*t8
targid=targid + −39.3371*t7*t9*t9
targid=targid + 3.2002*t9*t7*t7
targid=targid + −65.7963*t9*t8*t8
targid=targid + 34.5815*t8*t9*t9
targid=targid*0.8427 + 2.1317
print "targid = ", format$(targid,"0.000000")
end
11. Extract Candidate Target and determine if target exists and location
do i=0,n−1
   zj1(i)=real(nint(zj1(i)))
   if (zj1(i).gt.0 .and. zj1(i).lt.5)then
      zj1(i)=1
   else
      zj1(i)=0
   end if
enddo
12. Extract Cross-section slices
call slices(b,1,n,xp,nxp)
call slices(b,2,n,yp,nyp)
call slices(b,3,n,zp,nzp)
subroutine slices(A,icol,n,B,n1)
implicit none
integer i,icol,n,n1
integer A(0:n−1,0:2)
integer B(0:n−1)
integer z(0:n−1,0:2)
icol=icol−1
call csort2(A,icol,n,z)
n1=1
B(0)=z(0,icol)
do i=1,n−1
   if(z(i, icol). ne.B(n−1))then
      B(n1)=z(i,icol)
      n1 = n1 + 1
   endif
enddo
return
end
13. Apply Shape Characterizer
cls
on error resume next
input "S => ", S
avg0=0.5
dev0=0.5
S = (S − avg0) / dev0
input "N => ", N
avg1=4
dev1=2.2222
N = (N − avg1) / dev1
t1 = 0.5455
```

```
t1=t1 + -1.4983*N
t1=t1 + -0.404*N*N
t1=t1 + 0.5154*N*N*N
t2 = 0
t2=t2 + 0.2*S
t2=t2 + -0.2667*N
t3 = 0
t3=t3 + 0.2*S
t3=t3 + 0*S*S
t3=t3 + 0*S*S*S
t4 = -1.3457
t4=t4 + -1.2483*t1
t4=t4 + 0.9904*N
t4=t4 + 1.0176*t1*t1
t4=t4 + 1.8455*N*N
t4=t4 + 3.2656*t1*N
t4=t4 + 6.9251*t1*t1*t1
t4=t4 + -1.1587*N*N*N
t4=t4 + 5.3817*N*t1*t1
t4=t4 + -0.1932*t1*N*N
t5 = -1.319
t5=t5 + 0.1858*t1
t5=t5 + -1.4401*t3
t5=t5 + 1.1002*t1*t1
t5=t5 + 12.6254*t3*t3
t5=t5 + 1.4314*t1*t3
t5=t5 + 0.8973*t1*t1*t1
t5=t5 + 13.5737*t3*t3*t3
t5=t5 + 2.8124*t3*t1*t1
t5=t5 + -5.4825*t1*t3*t3
t6 = -0.6995
t6=t6 + -0.4762*t4
t6=t6 + 0.2221*t5
t6=t6 + -0.3014*t4*t4
t6=t6 + 0.1565*t5*t5
t6=t6 + 0.1268*t4*t5
t6=t6 + 0.3597*t4*t4*t4
t6=t6 + 0*t5*t5*t5
t6=t6 + -0.4057*t5*t4*t4
t6=t6 + 0.2608*t4*t5*t5
outval = t6*0.2778 + 0.1667
print "outval = ", format$(outval,"0.000000")
end
    14. Calculate Moments and Cumulants
    subroutine mean(A,n,meanA)
    implicit none
    integer n,i
    real A(0:n-1)
    real meanA
    meanA=0.0
    do i=0,n-1
       meanA=meanA+A(i)/n
    enddo
    return
    end
    subroutine stdev(A,n,stdevA)
    implicit none
    integer n,i
    real A(0:n-1)
    real stdevA,meanA,s,pp
    stdevA=0.0
    meanA=0.0
    do i=0,n-1
       meanA=meanA+A(i)/n
    enddo
    do i=0,n-1
       s=A(i)-meanA
       pp=s*s
       stdevA =stdevA+pp
    enddo
    stdevA=sqrt(stdevA/(n-1))
    return
    end
    subroutine skewness(A,n,ystat)
    implicit none
    integer n
    real A(0:n-1)
    integer i
    real ystat,ymean,ystdev
    call mean(A,n,ymean)
```

```
call stdev(A,n,ystdev)
ystat=0
do i=0,n−1
    ystat=ystat+(1/n)*((A(i)−ymean)/ystdev)**3
enddo
return
end
subroutine kurtosis(A,n,ystat)
implicit none
integer n
real A(0: n−1)
integer i
real ystat,ymean,ystdev
call mean(A,n,ymean)
call stdev(A,n,ystdev)
ystat=0
do i=0,n−1
    ystat=ystat+(1/n)*((A(i)−ymean)/ystdev)**4
enddo
ystatystat−3
return
end
15. Apply Square Shape Recognizer Data Model
cls
on error resume next
input "stdev => ", stdev
avg0=0
dev0=1
stdev =(stdev − avg0) / dev0
input "skew => ", skew
avg1=0
dev1=1
skew = (skew − avg1) / dev1
input "kurt => ", kurt
avg2=0
dev2=1
kurt = (kurt − avg2) / dev2
t1 = −8.7325
t1=t1 + 16.1062*stdev
t1=t1 + 7.7824*skew
t1=t1 + −4.2487*kurt
t1=t1 + −8.4543*stdev*stdev
t1=t1 + −1.0114*skew*skew
t1=t1 + −0.4265*kurt*kurt
t1=t1 + −11.0898*stdev*skew
t1=t1 + 5.6503*stdev*kurt
t1=t1 + 1.4876*skew*kurt
t1=t1 + −1.0844*stdev*skew*kurt
t1=t1 + 1.1564*stdev*stdev*stdev
t1=t1 + 0.0664*skew*skew*skew
t1=t1 + −0.012*kurt*kurt*kurt
t1=t1 + 3.9996*skew*stdev*stdev
t1=t1 + 0.6607*stdev*skew*skew
t1=t1 + 0.2972*stdev*kurt*kurt
t1=t1 + −1.8273*kurt*stdev*stdev
t1=t1 + −0.084*kurt*skew*skew
t1=t1 + 0.0594*skew*kurt*kurt
t2 = 0.499
t2=t2 + −0.0445*stdev
t2=t2 + 0.0027*skew
t2=t2 + 0.098*stdev*stdev
t2=t2 + −0.0018*skew*skew
t2=t2 + −0.0262*stdev*skew
t2=t2 + −0.0469*stdev*stdev*stdev
t2=t2 + −0.0032*skew*skew*skew
t2=t2 + 0.0116*skew*stdev*stdev
t2=t2 + 0.0099*stdev*skew*skew
squr = 1439.2517
squr=squr + −3245.4202*t1
squr=squr + 5.2508*kurt
squr=squr + −4734.6232*t2
squr=squr + 2159.0814*t1*t1
squr=squr + −0.0368*kurt*kurt
squr=squr + 6231.9075*t2*t2
squr=squr + −133.4063*t1*kurt
squr=squr + 6264.3623*t1*t2
squr=squr + 112.4382*kurt*t2
squr=squr + −1674.8553*t1*kurt*t2
squr=squr + −1172.5311*t1*t1*t1
squr=squr + 0*kurt*kurt*kurt
```

-continued

```
squr=squr + −3869.1525*t2*t2*t2
squr=squr + 971.6707*kurt*t1*t1
squr=squr + −0.0339*t1*kurt*kurt
squr=squr + −3049.0222*t1*t2*t2
squr=squr + −809.8377*t2*t1*t1
squr=squr + 0.1072*t2*kurt*kurt
squr=squr + 724.1183*kurt*t2*t2
print "squr = ", format$(squr,"0.000000")
end
    16. Apply Rectangle Shape Recognizer
    cls
    on error resume next
    input "stdev => ", stdev
    avg0=0
    dev0=1
    stdev = (stdev − avg0) / dev0
    input "skew => ", skew
    avg1=0
    dev1=1
    skew = (skew − avg1) / dev1
    input "kurt => ", kurt
    avg2=0
    dev2=1
    kurt = (kurt − avg2) / dev2
    t1 = 0.7139
    t1=t1 + −0.4487*stdev
    t1=t1 + −0.135*skew
    t1=t1 + 0.0548*kurt
    t1=t1 + 0.306*stdev*stdev
    t1=t1 + 0.0093*skew*skew
    t1=t1 + 0.0031*kurt*kurt
    t1=t1 + 0.209*stdev*skew
    t1=t1 + −0.089*stdev*kurt
    t1=t1 + −0.0084*skew*kurt
    t1=t1 + 0.0079*stdev*skew*kurt
    t1=t1 + −0.0685*stdev*stdev*stdev
    t1=t1 + −0.004*skew*skew*skew
    t1=t1 + 0.0001*kurt*kurt*kurt
    t1=t1 + −0.0796*skew*stdev*stdev
    t1=t1 + −0.0034*stdev*skew*skew
    t1=t1 + −0.0031*stdev*kurt*kurt
    t1=t1 + 0.0343*kurt*stdev*stdev
    t1=t1 + 0.0015*kurt*skew*skew
    t1=t1 + −0.0003*skew*kurt*kurt
    t2 = 0.5173
    t2=t2 + −0.0904*stdev
    t2=t2 + 0.0113*kurt
    t2=t2 + 0.1138*stdev*stdev
    t2=t2 + 0.0011*kurt*kurt
    t2=t2 + −0.024*stdev*kurt
    t2=t2 + −0.042*stdev*stdev*stdev
    t2=t2 + 0*kurt*kurt*kurt
    t2=t2 + 0.0122*kurt*stdev*stdev
    t2=t2 + −0.0011*stdev*kurt*kurt
    t3 = −77.6056
    t3=t3 + −18069.338*t1
    t3=t3 + 1558.8694*stdev
    t3=t3 + 14563.848*t2
    t3=t3 + −16865.123*t1*t1
    t3=t3 + 0.9483*stdev*stdev
    t3=t3 + −21107.108*t2*t2
    t3=t3 + 18605.424*t1*stdev
    t3=t3 + 52937.839*t1*t2
    t3=t3 + −24846.303*stdev*t2
    t3=t3 + −22824.812*t1*stdev*t2
    t3=t3 + −7165.8933*t1*t1*t1
    t3=t3 + −0.0009*stdev*stdev*stdev
    t3=t3 + 19184.557*t2*t2*t2
    t3=t3 + −7159.3752*stdev*t1*t1
    t3=t3 + −10.8134*t1*stdev*stdev
    t3=t3 + −109868.89*t1*t2*t2
    t3=t3 + 82565.844*t2*t1*t1
    t3=t3 + 8.9252*t2*stdev*stdev
    t3=t3 + 36230.44*stdev*t2*t2
    t4 = −173.1588
    t4=t4 + −1855.8662*t1
    t4=t4 + −19.0692*kurt
    t4=t4 + 2632.1107*t2
    t4=t4 + 4080.3157*t1*t1
    t4=t4 + 0.0104*kurt*kurt
```

```
t4=t4 + 2595.4904*t2*t2
t4=t4 + 239.0646*t1*kurt
t4=t4 + −7699.3372*t1*t2
t4=t4 + −162.953*kurt*t2
t4=t4 + 984.7128*t1*kurt*t2
t4=t4 + −3919.6113*t1*t1*t1
t4=t4 + 0*kurt*kurt*kurt
t4=t4 + −2885.6103*t2*t2*t2
t4=t4 + −731.566*kurt*t1*t1
t4=t4 + 0.0145*t1*kurt*kurt
t4=t4 + −3988.0655*t1*t2*t2
t4=t4 + 11124.641*t2*t1*t1
t4=t4 + −0.0352*t2*kurt*kurt
t4=t4 + −329.0933*kurt*t2*t2
t5 = 259.3714
t5=t5 + −859.0387*t4
t5=t5 + 40.2851*skew
t5=t5 + −30.9792*kurt
t5=t5 + 323.8594*t4*t4
t5=t5 + −2.8428*skew*skew
t5=t5 + −0.1779*kurt*kurt
t5=t5 + −152.5373*t4*skew
t5=t5 + 121.8502*t4*kurt
t5=t5 + 1.3911*skew*kurt
t5=t5 + −2.7864*t4*skew*kurt
t5=t5 + 717.4708*t4*t4*t4
t5=t5 + −0.0015*skew*skew*skew
t5=t5 + 0*kurt*kurt*kurt
t5=t5 + 143.9216*skew*t4*t4
t5=t5 + 5.6934*t4*skew*skew
t5=t5 + 0.3564*t4*kurt*kurt
t5=t5 + −119.7801*kurt*t4*t4
t5=t5 + 0.0011*kurt*skew*skew
t5=t5 + −0.0003*skew*kurt*kurt
rect = 180.678
rect=rect + −231.9235*t5
rect=rect + 27.3046*skew
rect=rect + −9.6504*kurt
rect=rect + −1234.8733*t5*t5
rect=rect + −2.1871*skew*skew
rect=rect + −0.1997*kurt*kurt
rect=rect + −103.8636*t5*skew
rect=rect + 36.9092*t5*kurt
rect=rect + 1.3074*skew*kurt
rect=rect + −2.6183*t5*skew*kurt
rect=rect + 1956.0207*t5*t5*t5
rect=rect + −0.0011*skew*skew*skew
rect=rect + 0*kurt*kurt*kurt
rect=rect + 98.4999*skew*t5*t5
rect=rect + 4.3798*t5*skew*skew
rect=rect + 0.4*t5*kurt*kurt
rect=rect + −35.2138*kurt*t5*t5
rect=rect + 0.001*kurt*skew*skew
rect=rect + −0.0003*skew*kurt*kurt
print "rect = ", format$(rect,"0.000000")
end
17. Apply Circle Shape Recognizer Data Model
cls
on error resume next
input "stdev => ", stdev
avg0=0
dev0=1
stdev = (stdev − avg0) / dev0
input "skew => ", skew
avg1=0
dev1=1
skew = (skew − avg1) / dev1
input "kurt => ", kurt
avg2=0
dev2=1
kurt = (kurt − avg2) / dev2
t1= 35.3015
t1=t1 + −10.3986*stdev
t1=t1 + −50.2487*skew
t1=t1 + 6.8536*kurt
t1=t1 + −2.5942*stdev*stdev
t1=t1 + 22.9365*skew*skew
t1=t1 + 0.4247*kurt*kurt
t1=t1 + 13.5646*stdev*skew
t1=t1 + −1.4197*stdev*kurt
```

-continued

```
t1=t1 + −6.3791*skew*kurt
t1=t1 + 1.0864*stdev*skew*kurt
t1=t1 + −0.1976*stdev*stdev*stdev
t1=t1 + −3.0322*skew*skew*skew
t1=t1 + 0.0082*kurt*kurt*kurt
t1=t1 + 2.2012*skew*stdev*stdev
t1=t1 + −5.0368*stdev*skew*skew
t1=t1 + −0.0547*stdev*kurt*kurt
t1=t1 + −0.2888*kurt*stdev*stdev
t1=t1 + 1.3431*kurt*skew*skew
t1=t1 + −0.1869*skew*kurt*kurt
t2 = 0.3476
t2=t2 + 0.319*stdev
t2=t2 + −0.0112*kurt
t2=t2 + −0.2213*stdev*stdev
t2=t2 + −0.0004*kurt*kurt
t2=t2 + 0.0166*stdev*kurt
t2=t2 + 0.0399*stdev*stdev*stdev
t2=t2 + 0*kurt*kurt*kurt
t2=t2 + −0.0019*kurt*stdev*stdev
t2=t2 + −0.0002*stdev*kurt*kurt
t3 = 20.2592
t3=t3 + 102.8048*t1
t3=t3 + −55.3313*stdev
t3=t3 + 10.0486*kurt
t3=t3 + −923.6519*t1*t1
t3=t3 + 32.9265*stdev*stdev
t3=t3 + 0.3638*kurt*kurt
t3=t3 + 265.0418*t1*stdev
t3=t3 + −33.2655*t1*kurt
t3=t3 + −8.0704*stdev*kurt
t3=t3 + 16.1045*t1*stdev*kurt
t3=t3 + 1277.8001*t1*t1*t1
t3=t3 + −0.0589*stdev*stdev*stdev
t3=t3 + 0*kurt*kurt*kurt
t3=t3 + −308.801*stdev*t1*t1
t3=t3 + −65.6686*t1*stdev*stdev
t3=t3 + −0.7262*t1*kurt*kurt
t3=t3 + 26.3573*kurt*t1*t1
t3=t3 + 0.014*kurt*stdev*stdev
t3=t3 + −0.001*stdev*kurt*kurt
t4 = 618.027
t4=t4 + −4441.4235*t1
t4=t4 + −154.6627*stdev
t4=t4 + 188.7003*skew
t4=t4 + 10005.74*t1*t1
t4=t4 + 66.6965*stdev*stdev
t4=t4 + 38.4076*skew*skew
t4=t4 + 1112.1743*t1*stdev
t4=t4 + −932.3528*t1*skew
t4=t4 + −117.027*stdev*skew
t4=t4 + 234.0486*t1*stdev*skew
t4=t4 + −7186.6583*t1*t1*t1
t4=t4 + −0.0295*stdev*stdev*stdev
t4=t4 + 0.004*skew*skew*skew
t4=t4 + −1605.2637*stdev*t1*t1
t4=t4 + −133.4835*t1*stdev*stdev
t4=t4 + −76.8216*t1*skew*skew
t4=t4 + 1109.94*skew*t1*t1
t4=t4 + 0.0506*skew*stdev*stdev
t4=t4 + −0.0234*stdev*skew*skew
circ = 249.5062
circ=circ + 85.1877*t3
circ=circ + −113.5633*stdev
circ=circ + −1071.3463*t4
circ=circ + 1361.5581*t3*t3
circ=circ + −0.6902*stdev*stdev
circ=circ + 180.1794*t4*t4
circ=circ + 1066.7217*t3*stdev
circ=circ + −600.4015*t3*t4
circ=circ + −607.0379*stdev*t4
circ=circ + −252.2958*t3*stdev*t4
circ=circ + −374.621*t3*t3*t3
circ=circ + 0*stdev*stdev*stdev
circ=circ + −169.8192*t4*t4*t4
circ=circ + −941.9394*stdev*t3*t3
circ=circ + 1.2513*t3*stdev*stdev
circ=circ + 4700.8014*t3*t4*t4
circ=circ + −4086.4429*t4*t3*t3
circ=circ + 0.1286*t4*stdev*stdev
```

-continued

```
circ=circ + 729.1219*stdev*t4*t4
print "circ = ", format$(circ,"0.000000")
end
```

18. Perform 3D primitive shape recognition (Volumetric) using Volumetric Shape Recognizer Data Model

```
cls
on error resume next
input "sqrrat => ", sqrrat
avg0=0.347346
dev0=0.257595
sqrrat = (sqrrat − avg0) / dev0
input "cirrat => ", cirrat
avg1=0.26136
dev1=0.299084
cirrat = (cirrat − avg1) / dev1
input "recrat => ", recrat
avg2=0.461342
dev2=0.286608
recrat = (recrat − avg2) / dev2
t1 = 2.140537
t1=t1 + −0.554984*sqrrat
t1=t1 + −1.486669*cirrat
t1=t1 + −1.961653*recrat
t1=t1 + −0.723202*sqrrat*sqrrat
t1=t1 + −2.23146*cirrat*cirrat
t1=t1 + −0.70339*recrat*recrat
t1=t1 + −0.986561*sqrrat*cirrat
t1=t1 + 0.384267*sqrrat*recrat
t1=t1 + −1.330231*cirrat*recrat
t1=t1 + 1.146032*sqrrat*cirrat*recrat
t1=t1 + 0.029627*sqrrat*sqrrat*sqrrat
t1=t1 + 0.790767*cirrat*cirrat*cirrat
t1=t1 + −0.203694*recrat*recrat*recrat
t1=t1 + 0.027664*cirrat*sqrrat*sqrrat
t1=t1 + 0.767389*sqrrat*cirrat*cirrat
t1=t1 + −0.034321*sqrrat*recrat*recrat
t1=t1 + 0.501569*recrat*sqrrat*sqrrat
t1=t1 + 0.319538*recrat*cirrat*cirrat
t1=t1 + −0.819217*cirrat*recrat*recrat
t2 = 1.377919
t2=t2 + 0.21651*sqrrat
t2=t2 + −15.398505*sqrrat
t2=t2 + 18.820342*recrat
t2=t2 + −0.410596*sqrrat*sqrrat
t2=t2 + 30.531425*sqrrat*sqrrat
t2=t2 + 42.929545*recrat*recrat
t2=t2 + 0.155626*sqrrat*sqrrat
t2=t2 + −0.038907*sqrrat*recrat
t2=t2 + −74.056914*sqrrat*recrat
t2=t2 + 17.119525*sqrrat*sqrrat*recrat
t2=t2 + 0.030897*sqrrat*sqrrat*sqrrat
t2=t2 + −44.89291*sqrrat*sqrrat*sqrrat
t2=t2 + 78.573052*recrat*recrat*recrat
t2=t2 + 2.52622*sqrrat*sqrrat*sqrrat
t2=t2 + −5.885253*sqrrat*sqrrat*sqrrat
t2=t2 + −11.905429*sqrrat*recrat*recrat
t2=t2 + −3.06317*recrat*sqrrat*sqrrat
t2=t2 + 166.10598*recrat*sqrrat*sqrrat
t2=t2 + −201.10207*sqrrat*recrat*recrat
t3 = 1.267654
t3=t3 + 0.184478*sqrrat
t3=t3 + −1.4849*sqrrat
t3=t3 + 0.210468*recrat
t3=t3 + −0.381928*sqrrat*sqrrat
t3=t3 + −2.981706*sqrrat*sqrrat
t3=t3 + −1.035758*recrat*recrat
t3=t3 + −0.249815*sqrrat*sqrrat
t3=t3 + 0.192463*sqrrat*recrat
t3=t3 + 0.46816*sqrrat*recrat
t3=t3 + 3.401237*sqrrat*sqrrat*recrat
t3=t3 + 0.047071*sqrrat*sqrrat*sqrrat
t3=t3 + 2.184666*sqrrat*sqrrat*sqrrat
t3=t3 + −0.838692*recrat*recrat*recrat
t3=t3 + 1.356104*sqrrat*sqrrat*sqrrat
t3=t3 + 2.039595*sqrrat*sqrrat*sqrrat
t3=t3 + −2.040051*sqrrat*recrat*recrat
t3=t3 + −0.677151*recrat*sqrrat*sqrrat
t3=t3 + 1.295684*recrat*sqrrat*sqrrat
t3=t3 + −0.225608*sqrrat*recrat*recrat
shape3d = 0.117942
```

```
shape3d=shape3d + 0.526004*t1
shape3d=shape3d + −1.047472*t2
shape3d=shape3d + 1.8487*t3
shape3d=shape3d + −0.320166*t1*t1
shape3d=shape3d + −0.587216*t2*t2
shape3d=shape3d + 3.452296*t3*t3
shape3d=shape3d + 1.66785*t1*t2
shape3d=shape3d + −1.0663*t1*t3
shape3d=shape3d + −3.00491*t2*t3
shape3d=shape3d + 3.183958*t1*t2*t3
shape3d=shape3d + −0.033971*t1*t1*t1
shape3d=shape3d + 2.711255*t2*t2*t2
shape3d=shape3d + 0.580184*t3*t3*t3
shape3d=shape3d + 2.056935*t2*t1*t1
shape3d=shape3d + −2.41716*t1*t2*t2
shape3d=shape3d + −0.908928*t1*t3*t3
shape3d=shape3d + −1.840469*t3*t1*t1
shape3d=shape3d + −7.163242*t3*t2*t2
shape3d=shape3d + 3.809345*t2*t3*t3
shape3d =shape3d*0.725898 + 2.565217
print "shape3d = ", format$(shape3d,"0.000000")
if int(shape3d)=1 then shape$= "shell"
if int(shape3d)=2 then shape$= "cylindrical"
if int(shape3d)=3 then shape$= "box-like"
if int(shape3d)=4 then shape$= "spherical"
if int(shape3d)=5 then shape$= "unrecognized (possibly multiple)"
if int(shape3d)<1 or int(shape3d)>5 then shape$= "no definite object"
end
  19. Calculate centroids and covariances
  call calccovar(f,n,gcov)
    if(gcov(0, 0).gt.sqrt(gcov1(0,0)) .or.
+   gcov(1,1).gt.sqrt(gcov1(1,1)))shape$="no definite object"
    nother = total_n_slices − nrectangles − ncircles − nsquares
    IF nother > nrectangles AND nother > ncircles AND nother > nsquares THEN
  shape$= "unrecognized (possibly multiple)"
    subroutine calccovar(A,n,covar1)
    implicit none
    integer n,i,m,j,k,l1,l2
    real A(0:31,0:31,0:n−1)
    real B(0:n−1,0:1)
    real covar(0:1,0:1)
    real covar1(0:1,0:1,0:n−1)
    do i=0,n−1
      m=0
      do j=0,31
        do k=0,31
          B(m,0)=j*A(j,k,i)
          B(m,1)=k*A(j,k,i)
          m=m+1
        enddo
      enddo
      call covarz(covar,B,2,m)
      do l1=0,1
        do l2=0,1
          covar1(l1,l2,i)=covar(l1,l2)
        enddo
      enddo
    enddo
    return
    end
```

The disclosed and other embodiments and the functional operations described in this specification can be implemented in digital electronic circuitry, or in computer software, firmware, or hardware, including the structures disclosed in this specification and their structural equivalents, or in combinations of one or more of them. The disclosed and other embodiments can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

The disclosed embodiments can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of what is disclosed here, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

A computer system for implementing the disclosed embodiments can include client computers (clients) and server computers (servers). A client and a server are generally remote from each other and typically interact through a communication network. The relationship of client and server can arise by virtue of computer programs running on the respective computers and having a client-server relationship to each other.

While this specification contains many specifics, these should not be construed as limitations on the scope of any invention or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, operations are depicted in the drawings in a particular order, and such operations should be performed in the particular order shown or in sequential order, and that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments have been described. Other embodiments are within the scope of the following claims.

What is claimed is:

1. A computer-automated method for processing muon vehicle imaging data of a vehicle under inspection located in a vehicle inspection region within a muon tomography vehicle imaging system, comprising:
    processing muon vehicle imaging data obtained from the vehicle inspection region to obtain a histogram of the muon vehicle imaging data at different positions in the vehicle inspection region;
    separating the muon vehicle imaging data into bins based on the histogram;
    removing a subset of the muon vehicle imaging data in a mode bin that has higher frequencies of occurrence than remaining muon vehicle imaging data from the muon vehicle imaging data to retain the remaining muon vehicle imaging data for further processing;
    using a vehicle assembly recognizer Data Model for identifying vehicle components from the remaining muon vehicle imaging data;
    applying the vehicle assembly recognizer Data Model to process the remaining muon vehicle imaging data to produce an image of the vehicle inspection region by removing vehicle components;
    using a target identification Data Model for identifying a target object from the remaining muon vehicle imaging data;
    applying the target identification Data Model to process data of the image produced after applying the vehicle assembly recognizer Data Model to produce an image of the target object; and
    processing the image of the target object to determine a location and a shape of the target object in the vehicle under inspection.

2. The method of claim 1, wherein:
    the processing of the image of the target object to determine a location and a shape of the target object in the vehicle under inspection comprises:
        extracting cross-section slices from the image of the target object, each cross-section slice having at least one data point in the image of the target object;

performing a 2-dimensional primitive shape detection algorithm to each slice to determine a 2-dimensional primitive shape of the target object in each slice; and processing 2-dimensional primitive shapes of the target object in the extracted cross-section slices to construct a 3-dimensional primitive shape representative of the shape of the target object in the vehicle under inspection.

3. The method of claim 2, wherein:

the performing of the 2-dimensional primitive shape detection algorithm to each slice to determine the 2-dimensional primitive shape of the target object in each slice comprises:

applying a plurality of primitive shape Data Models to process each slice to determine whether one or more of primitive shapes respectively corresponding to the primitive shape Data Models be present in each slice.

4. The method of claim 3, wherein:

the primitive shape Data Models comprise a Data Model for a square shape, a Data Model for a circle shape, and a Data Model for a rectangle shape.

5. The method of claim 4, comprising:

dividing each slice into a plurality of neighborhood regions; and processing each neighborhood region based on the primitive shape Data Models to determine presence of each primitive shape.

6. The method of claim 5, comprising:

using ratios of numbers of identified primitive shapes to numbers of neighborhood regions respectively corresponding to the identified primitive shapes to determine the shape of the target object in the vehicle under inspection.

7. The method of claim 3, wherein:

the performing of the 2-dimensional primitive shape detection algorithm to each slice to determine the 2-dimensional primitive shape of the target object in each slice comprises:

determining a covariance for a surface orientation for each slice.

8. The method of claim 1, comprising:

determining an optimal bin number for the bins.

9. A computer system for processing muon vehicle imaging data of a vehicle volume under inspection within a muon tomography vehicle imaging system, comprising:

means for processing muon vehicle imaging data obtained from the vehicle volume to obtain a histogram of the muon vehicle imaging data at different positions in a vehicle inspection region;

means for separating the muon vehicle imaging data into bins based on the histogram;

means for removing a subset of the muon vehicle imaging data in a mode bin that has higher frequencies of occurrence than remaining muon vehicle imaging data from the muon vehicle imaging data to retain the remaining muon vehicle imaging data for further processing;

means for using a background recognizer Data Model for identifying background structure from the remaining muon vehicle imaging data;

means for applying the background recognizer Data Model to process the remaining muon vehicle imaging data to produce an image of the vehicle inspection region by removing identified background structure;

means for using a target identification Data Model for identifying a target object from the remaining muon vehicle imaging data;

means for applying the target identification Data Model to process data of the image produced after applying the background recognizer Data Model to produce an image of the target object; and means for processing the image of the target object to determine a location and a shape of the target object in the vehicle volume.

10. The system as in claim 9, wherein:

the background recognizer Data Model is a vehicle assembly recognizer Data Model for identifying vehicle components as the background structure.

11. A computer program product, encoded on a computer-readable medium, operable to cause data processing apparatus to perform operations for processing muon vehicle imaging data of a vehicle under inspection located in a vehicle inspection region within a muon tomography vehicle imaging system, the operations comprising:

processing muon vehicle imaging data obtained from the vehicle inspection region to obtain a histogram of the muon vehicle imaging data at different positions in the vehicle inspection region;

separating the muon vehicle imaging data into bins based on the histogram;

removing a subset of the muon vehicle imaging data in a mode bin that has higher frequencies of occurrence than remaining muon vehicle imaging data from the original muon vehicle imaging data to retain the remaining muon vehicle imaging data for further processing;

using a vehicle assembly recognizer Data Model for identifying vehicle components from the remaining muon vehicle imaging data;

applying the vehicle assembly recognizer Data Model to process the remaining muon vehicle imaging data to produce an image of the vehicle inspection region by removing vehicle components;

using a target identification Data Model for identifying a target object from the remaining muon vehicle imaging data;

applying the target identification Data Model to process data of the image produced after applying the vehicle assembly recognizer Data Model to produce an image of the target object; and processing the image of the target object to determine a location and a shape of the target object in the vehicle under inspection.

12. A muon tomography vehicle imaging system, comprising:

a first set of muon detectors located on a first side of a vehicle inspection region holding a vehicle for inspection, the muon detectors measuring incident muons;

a second set of muon detectors located on a second side of the vehicle inspection region opposite to the first side to measure outgoing muons exiting the vehicle inspection region; and a muon tomography control module that receives detector outputs from the first and the second sets of muon detectors and processes the detector outputs to produce a 3-dimensional image of the vehicle inspection region, the muon tomography control module comprising a suspect object detection module for processing muon vehicle imaging data of the 3-dimensional image, the suspect object detection module operable to:

process muon vehicle imaging data obtained from the vehicle inspection region to obtain a histogram of the muon vehicle imaging data at different positions in the vehicle inspection region;

separate the muon vehicle imaging data into bins based on the histogram;

remove a subset of the muon vehicle imaging data in a mode bin that has higher frequencies of occurrence than remaining muon vehicle imaging data from the original muon vehicle imaging data to retain the remaining muon vehicle imaging data for further processing;

using a vehicle assembly recognizer Data Model for identifying vehicle components from the remaining muon vehicle imaging data;

apply the vehicle assembly recognizer Data Model to process the remaining muon vehicle imaging data to produce an image of the vehicle inspection region by removing vehicle components;

using a target identification Data Model for identifying a target object from the remaining muon vehicle imaging data;

apply the target identification Data Model to process data of the image produced after applying the vehicle assembly recognizer Data Model to produce an image of the target object; and process the image of the target object to determine a location and a shape of the target object in the vehicle under inspection.

13. The system of claim 12, wherein:

the processing of the image of the target object to determine a location and a shape of the target object in the vehicle under inspection comprises:

extracting cross-section slices from the image of the target object, each cross-section slice having at least one data point in the image of the target object;

performing a 2-dimensional primitive shape detection algorithm to each slice to determine a 2-dimensional primitive shape of the target object in each slice; and processing 2-dimensional primitive shapes of the target object in the extracted cross-section slices to construct a 3-dimensional primitive shape representative of the shape of the target object in the vehicle under inspection.

14. The system of claim 13, wherein:

the performing of the 2-dimensional primitive shape detection algorithm to each slice to determine the 2-dimensional primitive shape of the target object in each slice comprises:

applying a plurality of primitive shape Data Models to process each slice to determine whether one or more of primitive shapes respectively corresponding to the primitive shape Data Models be present in each slice.

15. The system of claim 14, wherein:

the primitive shape Data Models comprise a Data Model for a square shape, a Data Model for a circle shape, and a Data Model for a rectangle shape.

16. The system of claim 15, comprising:

dividing each slice into a plurality of neighborhood regions; and processing each neighborhood region based on the primitive shape Data Models to determine presence of each primitive shape.

17. The system of claim 12, comprising:

determining an optimal bin number for the bins.

18. A computer-automated method for processing muon vehicle imaging data from a muon tomography vehicle imaging system, comprising:

applying Data Models to process muon tomography vehicle image data to isolate one or more target objects from other objects in a vehicle volume under inspection by the muon tomography vehicle imaging system;

applying primitive shape recognition to cross-section slices of an image of the vehicle volume containing data points of the one or more target objects to identify predetermined primitive shapes; and processing identified primitive shapes to construct a 3-dimensional image of each target object.

19. The method as in claim 18, wherein:

the applying Data Models to process muon tomography vehicle image data to isolate one or more target objects from other objects comprises:

processing muon vehicle imaging data obtained from the vehicle volume to obtain a histogram of the muon vehicle imaging data at different positions in the vehicle volume;

separating the muon vehicle imaging data into bins based on the histogram;

removing a subset of the muon vehicle imaging data in a mode bin that has higher frequencies of occurrence than remaining muon vehicle imaging data from the muon vehicle imaging data to retain the remaining muon vehicle imaging data for further processing;

applying a background recognizer Data Model for identifying the other objects to process the remaining muon vehicle imaging data to produce an image of the vehicle volume by removing the identified other objects; and applying a target identification Data Model for identifying the one or more target objects to process data of the image produced after applying the background recognizer Data Model to produce an image of the one or more target objects.

20. A computer-implemented method for using natural cosmic muons as a radiation source to obtain muon tomographic images of a vehicle under inspection, comprising:

obtaining a cosmic muon tomography vehicle image of a vehicle under inspection;

processing vehicle voxel data of each obtained muon vehicle image to compute histogram of the vehicle voxel data of the obtained muon vehicle image;

applying statistical processing based on the histogram to the vehicle voxel data to use a Data Model to monitor one or more changes in the obtained muon vehicle image that trigger a tip-off condition indicative of presence of a target object in the obtained muon vehicle image; and determining a shape of the target object.

21. The method as in claim 20, wherein:

the shape of the target object is determined by:

extracting cross-section slices from the image of the target object, each cross-section slice having at least one data point in the image of the target object;

performing a 2-dimensional primitive shape detection algorithm to each slice to determine a 2-dimensional primitive shape of the target object in each slice; and processing 2-dimensional primitive shapes of the target object in the extracted cross-section slices to construct a 3-dimensional primitive shape representative of the shape of the target object in the vehicle under inspection.

22. The method of claim 21, wherein:

the performing of the 2-dimensional primitive shape detection algorithm to each slice to determine the 2-dimensional primitive shape of the target object in each slice comprises:

applying a plurality of primitive shape Data Models to process each slice to determine whether one or more of primitive shapes respectively corresponding to the primitive shape Data Models be present in each slice.

23. The method as in claim 20, comprising:
for a voxel that triggers the tip-off condition, applying the Data Model to selected neighboring voxels for the voxel to perform a shape detection in the selected neighboring voxels.

24. The method as in claim 23, comprising:
generating an overall shape of the target object represented by voxels that trigger the tip-off condition.

25. The method as in claim 23, wherein:
the shape detection includes operating Data Model shape detectors for detecting different primitive shapes to determine presence or absence of the primitive shapes.

* * * * *